United States Patent
Sun et al.

(10) Patent No.: US 11,732,064 B2
(45) Date of Patent: Aug. 22, 2023

(54) PROCESS FOR PREPARING FUNCTIONAL POLYMERS THROUGH ADDITION OF AMINO AND POLYMERYL GROUPS TO ALDEHYDE MOIETIES

(71) Applicant: Dow Global Technologies LLC, Midland, MI (US)

(72) Inventors: Lixin Sun, Sugar Land, TX (US); David D. Devore, Midland, MI (US)

(*) Notice: Subject to any disclaimer, the term of this patent is extended or adjusted under 35 U.S.C. 154(b) by 0 days.

(21) Appl. No.: 15/764,554

(22) PCT Filed: Sep. 28, 2016

(86) PCT No.: PCT/US2016/054190
§ 371 (c)(1),
(2) Date: Mar. 29, 2018

(87) PCT Pub. No.: WO2017/058921
PCT Pub. Date: Apr. 6, 2017

(65) Prior Publication Data
US 2018/0273654 A1    Sep. 27, 2018

Related U.S. Application Data

(60) Provisional application No. 62/234,890, filed on Sep. 30, 2015.

(51) Int. Cl.
C08F 4/52    (2006.01)
C08F 4/64    (2006.01)
(Continued)

(52) U.S. Cl.
CPC .............. *C08F 8/32* (2013.01); *C07C 209/66* (2013.01); *C07C 213/02* (2013.01); *C08F 8/28* (2013.01); *C08F 8/30* (2013.01); *C08F 110/14* (2013.01); *C08F 210/16* (2013.01); *C08F 4/65908* (2013.01); *C08F 4/65912* (2013.01); *C08F 2410/01* (2013.01); *C08F 2800/20* (2013.01); *C08F 2810/40* (2013.01)

(58) Field of Classification Search
CPC ...... C08F 8/12; C08F 8/30; C08F 8/32; C08F 10/00
See application file for complete search history.

(56) References Cited

U.S. PATENT DOCUMENTS

| 7,355,089 B2 | 4/2008 | Chang et al. |
| 7,897,698 B2 | 3/2011 | Johannsen et al. |

(Continued)

FOREIGN PATENT DOCUMENTS

| WO | 2005/090426 A1 | 9/2005 |
| WO | 2005/090427 A2 | 9/2005 |

(Continued)

OTHER PUBLICATIONS

M.R. Luderer et al., Tetrahedron: Aymmetry 2009, 20, 981-998.

(Continued)

*Primary Examiner* — Rip A Lee

(57) ABSTRACT

The present disclosure relates to a one-pot process for synthesizing functional compounds or functional polymers by reacting an aldehyde with an alkyl-zinc or polymeryl-zinc composition in the presence of a specific Lewis acid, wherein the reaction is rapid and facile at high temperatures.

12 Claims, 16 Drawing Sheets

$^{13}$C NMR of functionalized ethylene-octene copolymer in benzene at 60°C

(51) Int. Cl.
C08F 8/00 (2006.01)
C08F 8/32 (2006.01)
C07C 209/66 (2006.01)
C08F 110/14 (2006.01)
C08F 8/30 (2006.01)
C08F 210/16 (2006.01)
C08F 8/28 (2006.01)
C07C 213/02 (2006.01)
C08F 4/659 (2006.01)

(56) References Cited

U.S. PATENT DOCUMENTS

| | | | |
|---|---|---|---|
| 7,947,793 B2 | 5/2011 | Marchand et al. | |
| 8,058,373 B2 | 11/2011 | Stevens et al. | |
| 8,293,859 B2 | 10/2012 | Marchand et al. | |
| 8,476,366 B2 | 7/2013 | Walton et al. | |
| 8,501,885 B2 | 8/2013 | Arriola et al. | |
| 8,563,658 B2 | 10/2013 | Walton et al. | |
| 8,669,326 B2 * | 3/2014 | Hagadorn | C08L 23/10 525/157 |
| 8,686,087 B2 | 4/2014 | Li Pi Shan et al. | |
| 8,716,400 B2 | 5/2014 | Carnahan et al. | |
| 8,785,554 B2 | 7/2014 | Li Pi Shan et al. | |
| 8,822,598 B2 | 9/2014 | Li Pi Shan et al. | |
| 8,822,599 B2 | 9/2014 | Li Pi Shan et al. | |
| 2004/0143118 A1 | 7/2004 | Johnston | |
| 2006/0199930 A1 | 9/2006 | Li Pi Shan et al. | |
| 2007/0167578 A1 | 7/2007 | Arriola et al. | |
| 2008/0311812 A1 | 12/2008 | Arriola et al. | |

FOREIGN PATENT DOCUMENTS

| | | | |
|---|---|---|---|
| WO | 2007/035485 | A1 | 3/2007 |
| WO | 2009/012215 | A1 | 1/2009 |
| WO | 2014/105411 | A1 | 7/2014 |
| WO | 2016/028957 | A1 | 2/2016 |
| WO | 2016/028970 | A1 | 2/2016 |

OTHER PUBLICATIONS

M. Genov et al., Journal of Organometallic Chemistry 2008, 693, 2017-2020.
A. Metzger et al., Angew. Chem. Int. Ed. 2010, 49, 4665-4668.
L. Pisani et al., Tetrahedron: Asymmetry 2008, 19, 1784-1789.
W.A. Nugent, Organic Letters 2002, 4 (13), 2133-2136.
M. Larsson, et al., Tetrahedron 2004, 60, 10659-10669.
C. Binder and B. Singaram, Organic Preparation arid Procedures International, 2011, 43:139-208.
D. Seebach, Angew. Chem. Int. Ed., 2011, 50, 96-101.
B. Weidmann, D. Seebach, Angew. Chem. Int. Ed. Engl., 1983, 22, 31-45.
Yamakawa et al., J. Am. Chem. Soc., 1995, 117, 6327-6335.
Hevia et al., Dalton Trans., 2010, 39, 520-526.
Giacomelli et al., Journal of Organic Chemistry, 1974, 39, 2736-2740.
Lewinski et al., Angew, Chem. Int. Ed., 2010, 49, 8266-8269.
Costa et al, Tetrahedron, 2005, 61, 26, 6442-6446.
Franssen et al, Chem. Soc. Reviews, 2013, 42, 13, 5809-5832.
Ring, et al, Polymer Preprints, 2007, 48, 1, 961-962.
PCT/US2016/054190, International Search Report dated Apr. 6, 2017.
PCT/US2016/054190, Written Opinion of the International Search Authority dated Apr. 6, 2017.

* cited by examiner

GCMS of reaction products of benzaldehyde with ZnEt$_2$ at 1:2 molar ratio

GCMS of reaction products of benzaldehyde with ZnBu$_2$ with 10 mol% DMAE

GCMS of reaction products of benzaldehyde with ZnBu$_2$ at 1:2 molar ratio with no promoter GCMS of reaction products of tBu-benzaldehyde with ZnEt$_2$ at tBu-benzaldehyde:ZnEt$_2$ ratio of 1:1.67

GCMS of reaction products of tBu-benzaldehyde with ZnEt$_2$ at a tBu-benzaldehyde: ZnEt$_2$ ratio of 1:0.4

MW: 162.23
1

MW: 164.24
2

MW: 192.30
3

MW: 190.28
4

Possible pathway to form compounds 2 and 4 via MPV reduction

Possible pathway to form compound 5

GCMS scan of compound 6

GCMS scan of compound 7

¹H NMR of Hexyloxyethylzinc

MW: 219.37
6

MW: 247.42
7

¹H NMR spectra of compounds 6 and 7

13C NMR spectrum of compound 7

(1)

(2)

GCMS of allyloxy containing product

GCMS of vinyl containing products

$^1$H NMR spectra of allyloxy-containing products

$^1$H NMR spectra of vinyl-containing products

¹H NMR spectra of functionalized polyoctene (1), comparative polyoctene (2) and functionalized model compound (3); arrows indicate peaks of the functionalized amino groups $^1$H NMR spectra of functionalized polyoctene (1), comparative polyoctene (2) and functionalized model compound (3); arrows indicate the peaks of the unreacted aldehyde 13C NMR of functionalized ethylene-octene copolymer in benzene at 60°C

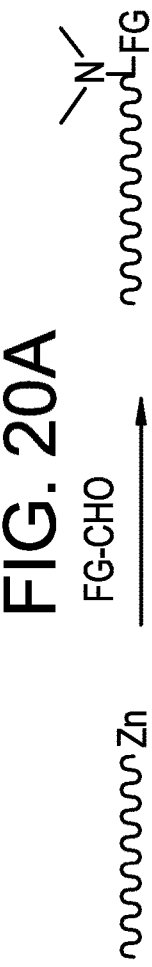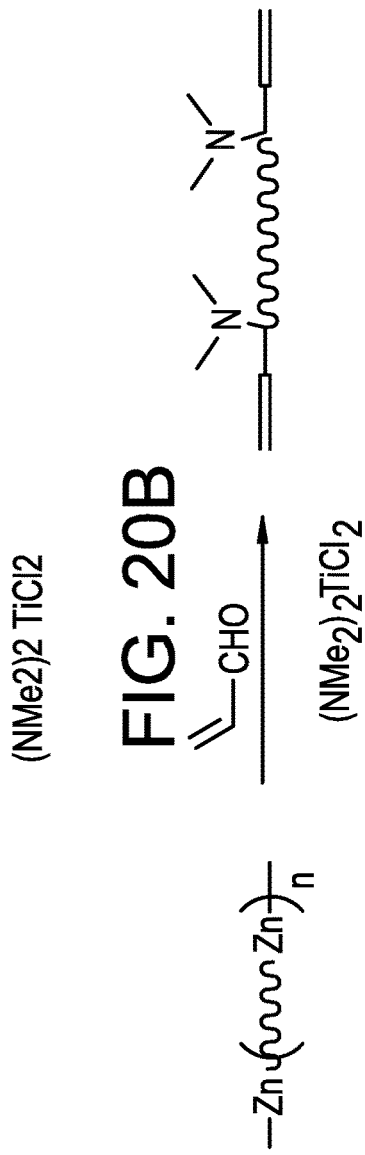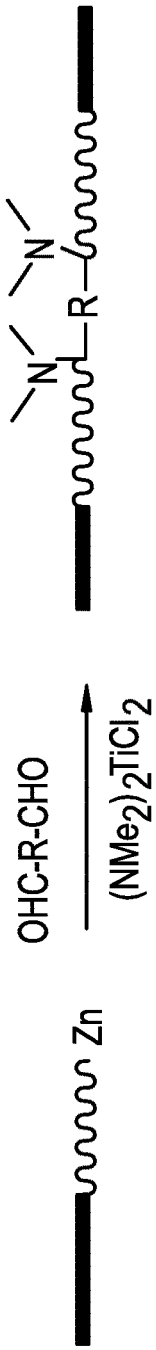

PROCESS FOR PREPARING FUNCTIONAL POLYMERS THROUGH ADDITION OF AMINO AND POLYMERYL GROUPS TO ALDEHYDE MOIETIES

FIELD

Embodiments relate to a one-pot process for producing functional polymers. In one aspect, embodiments relate to a facile, one-pot reaction for synthesizing functional polymers through addition of amino and polymeryl groups to aldehyde moieties.

INTRODUCTION

High molar mass polymers, such as polyolefins, are useful materials. For example, the high chemical and oxidation resistance coupled with the competitive prices of saturated polyolefin materials make polyolefins highly desirable to the plastics industry. It has been demonstrated that controlled inclusion of functional groups on polymers, such as polyolefins, can lead to property enhancements. However, precise and controlled functionalization has been challenging. Most methods for incorporation of reactive groups in polyolefins involve post-polymerization reactions, which generally have poor control over the functionalization location and quantity and leads to diminished mechanical properties.

Recently, advances in chain shuttling technology and coordinative chain transfer polymerization technology have provided unique opportunities to develop functionalized polymers and polyolefins that are not limited to post-polymerization reactions. For example, one area of potential interest that has not been heavily investigated is the feasibility of functionalizing the polymeryl-zinc resulting from chain shuttling and coordinative chain transfer polymerization technologies via transformation of the polymeryl-zinc through addition to aldehyde moieties. However, significant challenges exist for developing a practical way for such a transformation in existing solution processes. Indeed, while chemical literature has described the addition reaction of dialkyl-zinc to aldehydes, this described reaction is not adaptable for existing solution processes, since it is limited to forming enantioselective secondary alcohols, requires low temperature for extended periods of time, requires excess amounts of dialkyl-zinc, and exhibits addition of only one of the two alkyl groups from the zinc to the aldehyde. Accordingly, a need exists for a practical process for producing functional polymers or polyolefins that is adaptable for existing solution processes for commercial applications.

SUMMARY

In certain embodiments, the present disclosure relates to a one-pot process for synthesizing functional polymers by reacting an aldehyde with an alkyl-zinc or polymeryl-zinc composition in the presence of an effective promoter for the reaction. In certain embodiments, the present disclosure relates to a one-pot process for synthesizing functional polymers by reacting an aldehyde with an alkyl-zinc or polymeryl-zinc composition in the presence of a Lewis acid promoter. In certain embodiments, the present disclosure relates to a one-pot process for synthesizing functional polymers by reacting an aldehyde with an alkyl-zinc or polymeryl-zinc composition in the presence of a Lewis acid promoter, wherein the reaction is rapid and facile at high temperatures.

In further embodiments, the present disclosure relates to a one-pot process for synthesizing functional polymers by reacting an aldehyde with a polymeryl-zinc composition in the presence of a Lewis acid promoter, wherein the polymeryl-zinc composition is a polymer composition formed by a polymerization process. In further embodiments, the present disclosure relates to a one-pot process for synthesizing functional polymers by reacting an aldehyde with a polymeryl-zinc composition in the presence of a Lewis acid promoter, wherein the polymeryl-zinc composition is a polymer composition formed by a polymerization process, the polymerization process comprising: contacting at least one addition polymerizable monomer with a catalyst composition under polymerization conditions, the catalyst composition comprising the contact product of at least one catalyst precursor, at least one co-catalyst, and at least one chain shuttling agent.

BRIEF DESCRIPTION OF THE DRAWINGS

FIG. 20 portrays non-limiting examples of functional polymers or polyolefins prepared by the simple, one-pot reaction of the present disclosure.

DETAILED DESCRIPTION

Figure 1A:
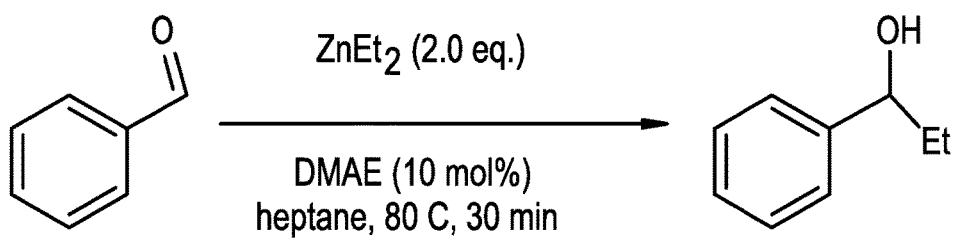
FIG. 1 portrays reactions of aldehyde and alkyl-zinc in the presence of a simple β-amino-alcohol promoter, dimethylaminoethanol (DMAE).

Embodiments relate to a one-pot process for synthesizing functional polymers through addition of alkyl-zinc or polymeryl-zinc to aldehyde moieties in the presence of an effective promoter for the reaction.

Definitions

All references to the Periodic Table of the Elements refer to the Periodic Table of the Elements published and copyrighted by CRC Press, Inc., 1990. Also, any references to a Group or Groups shall be to the Group or Groups reflected in this Periodic Table of the Elements using the IUPAC system for numbering groups. Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent U.S. version is so incorporated by reference in its entirety), especially with respect to the disclosure of synthetic techniques, product and processing designs, polymers, catalysts, definitions (to the extent not inconsistent with any definitions specifically provided in this disclosure), and general knowledge in the art.

"Functional polymer" refers to a polymer containing at least one reactive functional group. Such a polymer is, therefore, capable of entering into further polymerization or other reactions through its reactive functional group(s). Non-limiting examples of functional polymers, as defined herein, include polymers or polyolefins containing functional groups, polymers or polyolefins containing terminal functional groups on one end or both ends, telechelic polymers containing terminal functional groups on both ends possessing the same functionality, olefin/non-olefin diblock copolymers containing functional groups, and hard-soft-hard triblock copolymers containing functional groups.

"Zinc composition" refers to an alkyl-zinc or polymeryl-zinc composition. "Alkyl-zinc" or "alkyl-zinc composition" refer to compounds having the formula $ZnR'_2$ or $R^1Zn[R'Zn—]_YR^1$, wherein R' is an alkyl group, Y, on average, in each occurrence is a number from 1-150, inclusive, and $R^1$ in each occurrence is independently selected from alkyl, hydrogen, halide, amide, hydrocarbyl, hydrocarbylamide, dihydrocarbylamide, hydrocarbyloxide, hydrocarbylsulfide, dihydrocarbylphosphido, tri(hydrocarbyl)silyl; any hydrocarbyl group being optionally substituted with at least one halide, amide, hydrocarbylamide, dihydrocarbylamide, or hydrocarbyloxide; and each carbon-containing $R^1$ having from 1 to 50 carbon atoms, inclusive. "Polymeryl-zinc" or "polymeryl-zinc composition" refer to compounds having the formula $ZnR'_2$ or $R^1Zn[R'Zn—]_YR^1$, wherein R' is a polymer composition, Y, on average, in each occurrence is a number from 1-150, inclusive, and $R^1$ in each occurrence is independently selected from a polymer composition, alkyl, hydrogen, halide, amide, hydrocarbyl, hydrocarbylamide, dihydrocarbylamide, hydrocarbyloxide, hydrocarbylsulfide, dihydrocarbylphosphido, tri(hydrocarbyl)silyl; any hydrocarbyl group being optionally substituted with at least one halide, amide, hydrocarbylamide, dihydrocarbylamide, or hydrocarbyloxide; and each carbon-containing $R^1$ having from 1 to 50 carbon atoms, inclusive. "Polymer composition" is a polymer prepared by polymerizing any suitable addition polymerizable monomer by any polymerization method known to a person of ordinary skill in the art; the polymer composition may also be a polymer prepared by a polymerization process, the polymerization process comprising: contacting at least one addition polymerizable monomer with a catalyst composition under polymerization conditions, the catalyst composition comprising the contact product of at least one catalyst precursor, at least one co-catalyst, and at least one chain shuttling agent. Exemplary, non-limiting polymerization processes include those disclosed in U.S. Pat. No. 8,501,885 B2, as well as those known in the art for producing random copolymers. Exemplary, non-limiting polymerization processes include those conducted in a single reactor or two reactors.

The term "shuttling agent" or "chain shuttling agent" refers to a compound or mixture of compounds that is capable of causing polymeryl transfer between various active catalyst sites under conditions of polymerization. That is, transfer of a polymer fragment occurs both to and from an active catalyst site in a facile and reversible manner. In contrast to a shuttling agent or chain shuttling agent, an agent that acts merely as a chain transfer agent, such as some main-group alkyl compounds, may exchange, for example, an alkyl group on the chain transfer agent with the growing polymer chain on the catalyst, which generally results in termination of the polymer chain growth. In this event, the main-group center may act as a repository for a dead polymer chain, rather than engaging in reversible transfer with a catalyst site in the manner in which a chain shuttling agent does. Desirably, the intermediate formed between the chain shuttling agent and the polymeryl chain is not sufficiently stable relative to exchange between this intermediate and any other growing polymeryl chain, such that chain termination is relatively rare.

"Shuttling agent" or "chain shuttling agent" refer to those known in the art, including multi- or dual-headed chain shuttling agents, such as those disclosed in U.S. Pat. No. 8,501,885 B2, as well as those known in the art. The terms "dual-headed" or "multi-headed" refer to a compound or molecule containing more than one chain shuttling moiety joined by a polyvalent linking group. By way of illustration only, one example of a dual-headed CSA is provided in the compounds of the general formulas $R^1—[Zn—R^2—]_NZn—R^1$ or $R^1—[AlR^1—R^2—]_NAlR^1_2$, in which $R^1$ is a monovalent hydrocarbyl group and $R^2$ is a divalent hydrocarbadiyl group. In practice, suitable chain shuttling moieties typically include metal centers derived from a metal selected from Groups 2-14 of the Periodic Table of the Elements and having one or more available valencies capable of reversibly binding a growing polymer chain prepared by a coordination polymerization catalyst. At the same time that the chain shuttling moiety binds to the growing polymer chain, the remnant of the polyvalent linking group remaining after loss of the chain shuttling moiety or moieties incorporates or otherwise bonds to one or more active catalyst sites, thereby forming a catalyst composition containing an active coordination polymerization site capable of polymer insertion at one terminus of what was originally the polyvalent linking group. Shuttling of the new polymer chain attached to the linking group back to the chain shuttling moiety effectively grows a fraction of polymer chains containing a linking group and attached to a main group metal CSA at both ends.

"Catalyst precursors" include those known in the art and those disclosed in WO 2005/090426, WO 2005/090427, WO 2007/035485, WO 2009/012215, WO 2014/105411, U.S. Patent Publication Nos. 2006/0199930, 2007/0167578, 2008/0311812, and U.S. Pat. Nos. 7,355,089 B2, 8,058,373 B2, and 8,785,554 B2, all of which are incorporated herein by reference in their entirety. The terms "transition metal catalysts," "transition metal catalyst precursors," "catalysts," "catalyst precursors," "polymerization catalysts or catalyst precursors," and like terms are to be interchangeable in the present disclosure.

"Transition metal catalysts" include, for example, metal complexes serving as catalysts or catalyst precursors disclosed in WO 2005/090426, WO 2005/090427, WO 2009/012215, U.S. Patent Publication Nos. 2006/0199930, 2007/0167578, 2008/0311812, and U.S. Pat. No. 7,355,089 B2, as well as those known in the art. Among other things, this disclosure provides a catalyst composition and various methods that include at least one polymerization catalyst or catalyst precursor, at least one co-catalyst, and at least one chain shuttling agent as described above. This disclosure also provides a catalyst composition and various methods that include at least one polymerization catalyst or catalyst precursor, at least one co-catalyst, and at least one chain shuttling agent as described above, wherein the at least one polymerization catalyst or catalyst precursor is also a catalyst or catalyst precursor for preparing the at least one chain shuttling agent. Suitable catalysts or catalyst precursors for use in the methods and compositions disclosed herein include any compound or combination of compounds that is adapted for preparing polymers of the desired composition or type. Both heterogeneous and homogeneous catalyst may be employed. Examples of heterogeneous catalysts include the well-known Ziegler-Natta compositions, including the Group 4 metal halides and their derivatives, and including Group 4 metal halides supported on Group 2 metal halides or mixed halides and alkoxides, including the well-known chromium- or vanadium-based catalysts. However, for ease of use and for production of narrow molecular weight polymer segments in solution, especially useful catalysts include the homogeneous catalysts including a relatively pure organometallic compound or metal complex, especially compounds or complexes based on metals selected from Groups 3-15 or the Lanthanide series of the Periodic Table of the Elements.

"Co-catalyst" refers to those known in the art, e.g., those disclosed in U.S. Pat. No. 8,501,885 B2, that can activate the catalyst precursor to form an active catalyst composition.

"Solvent" refers to those known in the art and those known as appropriate by one of ordinary skill in the art for the present disclosures. Suitable solvents include aromatic hydrocarbons, such as toluene, and aliphatic hydrocarbons, such as Isopar™ and heptane.

"Polymer" refers to a compound prepared by polymerizing monomers, whether of the same or a different type. The generic term polymer thus embraces the term homopolymer, usually employed to refer to polymers prepared from only one type of monomer, and the term interpolymer as defined below. It also embraces all forms of interpolymers, e.g., random, block, homogeneous, heterogeneous, etc.

"Interpolymer" and "copolymer" refer to a polymer prepared by the polymerization of at least two different types of monomers. These generic terms include both classical copolymers, i.e., polymers prepared from two different types of monomers, and polymers prepared from more than two different types of monomers, e.g., terpolymers, tetrapolymers, etc.

The term "block copolymer" or "segmented copolymer" refers to a polymer comprising two or more chemically distinct regions or segments (referred to as "blocks") joined in a linear manner, that is, a polymer comprising chemically differentiated units which are joined (covalently bonded) end-to-end with respect to polymerized functionality, rather than in pendent or grafted fashion. The blocks differ in the amount or type of comonomer incorporated therein, the density, the amount of crystallinity, the type of crystallinity (e.g., polyethylene versus polypropylene), the crystallite size attributable to a polymer of such composition, the type or degree of tacticity (isotactic or syndiotactic), regio-regularity or regio-irregularity, the amount of branching, including long chain branching or hyper-branching, the homogeneity, and/or any other chemical or physical property. The block copolymers are characterized by unique distributions of both polymer polydispersity (PDI or Mw/Mn) and block length distribution, e.g., based on the effect of the use of a shuttling agent(s) in combination with catalysts.

Suitable "addition polymerizable monomers," as it relates to the definition of R' in connection with "polymer composition," include any addition polymerizable monomer, generally any olefin or diolefin monomer. Suitable monomers can be linear, branched, acyclic, cyclic, substituted, or unsubstituted. In one aspect, the olefin can be any α-olefin, including, for example, ethylene and at least one different copolymerizable comonomer, propylene and at least one different copolymerizable comonomer having from 4 to 20 carbons, or 4-methyl-1-pentene and at least one different copolymerizable comonomer having from 4 to 20 carbons. Examples of suitable monomers include, but are not limited to, straight-chain or branched α-olefins having from 2 to 30 carbon atoms, from 2 to 20 carbon atoms, or from 2 to 12 carbon atoms. Specific examples of suitable monomers include, but are not limited to, ethylene, propylene, 1-butene, 1-pentene, 3-methyl-1-butene, 1-hexane, 4-methyl-1-pentene, 3-methyl-1-pentene, 1-octene, 1-decene, 1-dodecene, 1-tetradecene, 1-hexadecene, 1-octadecene, and 1-eicosene. Suitable monomers for use in preparing the copolymers disclosed herein also include cycloolefins having from 3 to 30, from 3 to 20 carbon atoms, or from 3 to 12 carbon atoms. Examples of cycloolefins that can be used include, but are not limited to, cyclopentene, cycloheptene, norbornene, 5-methyl-2-norbornene, tetracyclododecene, and 2-methyl-1,4,5,8-dimethano-1,2,3,4,4a,5, 8,8a-octahydronaphthalene. Suitable monomers for preparing the copolymers disclosed herein also include di- and poly-olefins having from 3 to 30, from 3 to 20 carbon atoms, or from 3 to 12 carbon atoms. Examples of di- and poly-olefins that can be used include, but are not limited to, butadiene, isoprene, 4-methyl-1,3-pentadiene, 1,3-pentadiene, 1,4-pentadiene, 1,5-hexadiene, 1,4-hexadiene, 1,3-hexadiene, 1,3-octadiene, 1,4-octadiene, 1,5-octadiene, 1,6-octadiene, 1,7-octadiene, ethylidene norbornene, vinyl norbornene, dicyclopentadiene, 7-methyl-1,6-octadiene, 4-ethylidene-8-methyl-1,7-nonadiene, and 5,9-dimethyl-1,4,8-decatriene. In a further aspect, aromatic vinyl compounds also constitute suitable monomers for preparing the copolymers disclosed here, examples of which include, but are not limited to, mono- or poly-alkylstyrenes (including styrene, o-methylstyrene, m-methylstyrene, p-methylstyrene, o,p-dimethylstyrene, o-ethylstyrene, m-ethylstyrene and p-ethylstyrene), and functional group-containing derivatives, such as methoxystyrene, ethoxystyrene, vinylbenzoic acid, methyl vinylbenzoate, vinylbenzyl acetate, hydroxystyrene, o-chlorostyrene, p-chlorostyrene, divinylbenzene, 3-phenylpropene, 4-phenylpropene and α-methylstyrene, vinylchloride, 1,2-difluoroethylene, 1,2-dichloroethylene, tetrafluoroethylene, and 3,3,3-trifluoro-1-propene, provided the monomer is polymerizable under the conditions employed.

Further, in one aspect, suitable monomers or mixtures of monomers for use in combination with at least one chain shuttling agent include ethylene; propylene; mixtures of ethylene with one or more monomers selected from propylene, 1-butene, 1-hexene, 4-methyl-1-pentene, 1-octene, and styrene; and mixtures of ethylene, propylene and a conjugated or non-conjugated diene. In this aspect, "polymer composition" can be a copolymer or interpolymer containing two or more intramolecular regions comprising differing chemical or physical properties, especially regions of differentiated comonomer incorporation, joined in a dimeric, linear, branched or polybranched polymer structure. Such polymer compositions may be prepared by altering the polymerization conditions during a polymerization that includes a chain shuttling agent, for example by using two reactors with differing comonomer ratios, multiple catalysts with differing comonomer incorporation abilities, or a combination of such process conditions, and optionally a polyfunctional coupling agent.

Utilizing the polymerization processes disclosed here, polymer compositions, including block copolymers of one or more olefin monomers having the present molecular weight distribution, are readily prepared. Desirable polymer compositions comprise in polymerized form at least one monomer selected from ethylene, propylene, and 4-methyl-1-pentene. Highly desirably, the polymer compositions are interpolymers comprising in polymerized form ethylene, propylene, or 4-methyl-1-pentene and at least one different $C_{2-20}$ α-olefin comonomer, and optionally one or more additional copolymerizable comonomers. Suitable comonomers are selected from diolefins, cyclic olefins, and cyclic diolefins, halogenated vinyl compounds, vinylidene aromatic compounds, and combinations thereof. Generally preferred polymers are interpolymers of ethylene with 1-butene, 1-hexene or 1-octene. Desirably, the polymer compositions disclosed here have an ethylene content from 1 to 99 percent, a diene content from 0 to 10 percent, and a styrene and/or $C_{3-8}$ α-olefin content from 99 to 1 percent, based on the total weight of the polymer. Typically, the polymers of the disclosure have a weight average molecular weight (Mw) from 10,000 to 2,500,000.

The polymer compositions prepared according to this disclosure can have a melt index, $I_2$, from 0.01 to 2000 g/10 minutes, typically from 0.01 to 1000 g/10 minutes, more typically from 0.01 to 500 g/10 minutes, and especially from 0.01 to 100 g/10 minutes. Desirably, the disclosed polymer compositions can have molecular weights, $M_w$, from 1,000 g/mole to 5,000,000 g/mole, typically from 1000 g/mole to 1,000,000, more typically from 1000 g/mole to 500,000 g/mole, and especially from 1,000 g/mole to 300,000 g/mole. The density of the polymer compositions of this disclosure can be from 0.80 to 0.99 g/cm³ and typically, for ethylene containing polymers, from 0.85 g/cm³ to 0.97 g/cm³.

The polymer compositions according to this disclosure may be differentiated from conventional, random copolymers, physical blends of polymers, and block copolymers prepared via sequential monomer addition, fluxional catalysts, or by anionic or cationic living polymerization techniques, by, among other things, their narrow molecular weight distributions. In this aspect, for example, the polymer composition prepared according to this disclosure can be characterized by a polydispersity index (PDI) of from 1.5 to 3.0. For example, the polydispersity index (PDI) of the polymer composition can be from 1.5 to 2.8, from 1.5 to 2.5, or from 1.5 to 2.3.

If present, the separate regions or blocks within each polymer composition are relatively uniform, depending on the uniformity of reactor conditions, and chemically distinct from each other. That is, the comonomer distribution, tacticity, or other property of segments within the polymer are relatively uniform within the same block or segment. However, the average block length can be a narrow distribution, but is not necessarily so. The average block length can also be a most probable distribution.

In a further aspect, the resulting polymer composition may be linear or contain one or more branching centers, depending on whether a two-centered-, three-centered-, or higher centered shuttling agent is employed. Desirably, these interpolymers can be characterized by terminal blocks or segments of polymer having higher tacticity or crystallinity from at least some remaining blocks or segments. Even more desirably, the polymer can be a triblock copolymer containing a central polymer block or segment that is relatively amorphous or even elastomeric.

The polymer compositions of the present disclosure may be block interpolymers that can be characterized by an average block index, e.g., as discussed in U.S. Pat. Nos. 7,947,793, 7,897,698, and 8,293,859. The polymer compositions of the present disclosure may be block composites that can be characterized by a block composite index, e.g., as discussed in U.S. Pat. Nos. 8,563,658, 8,476,366, 8,686,087, and 8,716,400. The polymer compositions of the present disclosure may be crystalline block composites that can be characterized by a crystalline block composite index, e.g., as discussed in U.S. Pat. Nos. 8,785,554, 8,822,598, and 8,822,599. The polymer compositions of the present disclosure may be specified block composites that can be characterized by a microstructure index, e.g., as discussed in PCT/US15/046002. The polymer compositions of the present disclosure may be specified block composites that can be characterized by a modified block composite, e.g., as discussed in PCT/US15/046031.

Addition of Alkyl-Zinc to Aldehydes in the Presence of Chiral Beta-Amino Alcohol As noted above, the addition of dialkyl-zinc to aldehydes to form enantioselective secondary alcohols is known in literature (see, e.g., Luderer et al., *Tetrahedron: Asymmetry* 2009, 20, 981-998; Genov et al., *Journal of Organometallic Chemistry* 2008, 693, 2017-2020; Metzger et al., *Angew. Chem. Int. Ed.* 2010, 49, 4665-4668; Pisani et al., *Tetrahedron: Asymmetry* 2008, 19, 1784-1789; Nugent, *Organic Letters* 2002, 4 (13), 2133-2136; Larsson, et al., *Tetrahedron* 2004, 60, 10659-10669; Binder et al., *Organic Preparation and Procedures International*, 2011, 43:139-208; Yamakawa et al., *J. Am. Chem. Soc.*, 1995, 117, 6327; Hevia et al., *Dalton Trans.*, 2010, 39, 520; Giacomelli et al., *J. Org. Chem.*, 1974, 39, 2736). Such an addition reaction is shown below.

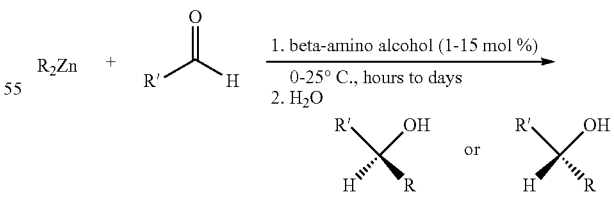

However, this reaction typically requires low temperature (0 to 25° C.) for extended periods of time (hours to days) in the presence of chiral β-amino-alcohol promoters. In addition, such a reaction requires excess amounts of dialkyl-zinc, and usually only one of the two alkyl groups reacts. Moreover, dimethyl-zinc and diethyl-zinc are the most commonly used alkyl-zinc with few higher carbon-containing zinc compounds reported due to the increased probability of β-hydride elimination resulting in reduction of aldehyde instead of alkylation, as demonstrated below.

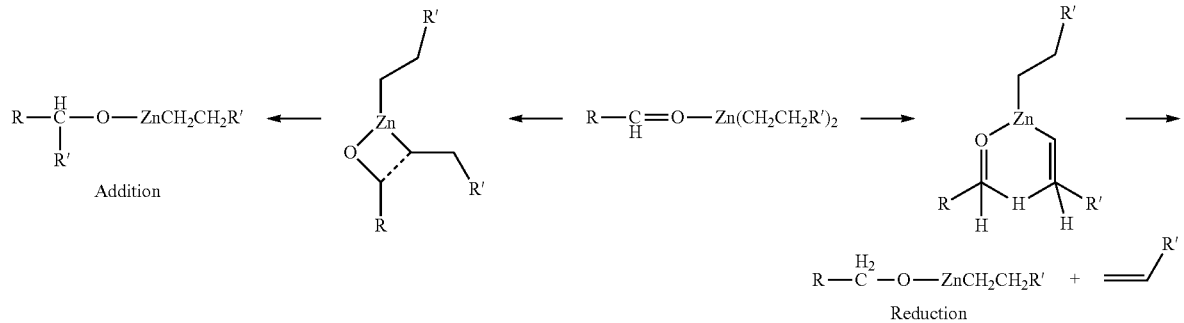

Accordingly, although the above reaction described in literature demonstrates the transfer of an alkyl group to the aldehyde without the undesired reductive elimination reaction, this reaction has limited utility for alkyl-zinc and polymeryl-zinc functionalization, since it does not meet basic requirements for application in existing olefin polymerization solution processes in a commercial plant setting. In other words, there is still a need for a practical process for functionalizing alkyl-zinc and polymeryl-zinc via addition to aldehyde in existing solution processes (1) that demonstrates the transfer of alkyl/polymer groups to the aldehyde without the undesired reductive elimination reaction, (2) that is facile at high temperatures (e.g., at least above the melting point of the polymers), (3) that can be completed in a reasonably short amount of time (e.g., minutes), and, (4) in the instances in which the alkyl-zinc or polymeryl-zinc has the formula $ZnR'_2$, where both alkyl/polymer groups attached to zinc are reacted. With regard to (4), both alkyl/polymer groups of $ZnR'_2$ would need to react in order to functionalize all of the alkyl/polymer R' groups. If only one alkyl/polymer group reacts, only 50% of the alkyl/polymer R' groups will be functionalized.

Addition of Alkyl-Zinc to Aldehydes in the Presence of Simple Beta-Amino Alcohol In view of the limited utility of the above reaction disclosed in literature, the present inventors evaluated the use of a simple β-amino-alcohol promoter, dimethylaminoethanol (DMAE), for functionalizing alkyl-zinc via addition of alkyl-zinc to aldehydes in existing solution processes. The reaction was conducted at 80° C., as it was considered the minimum temperature required to be adaptable to the solution process and to maintain the polymer solubility. Solvents used in this study were limited to aromatic and aliphatic hydrocarbons. The reaction was quenched with water and the conversion was estimated by integrating the area of GCMS (Gas Chromatography Mass Spectroscopy) peaks obtained via the method described below.

Figure 1B:
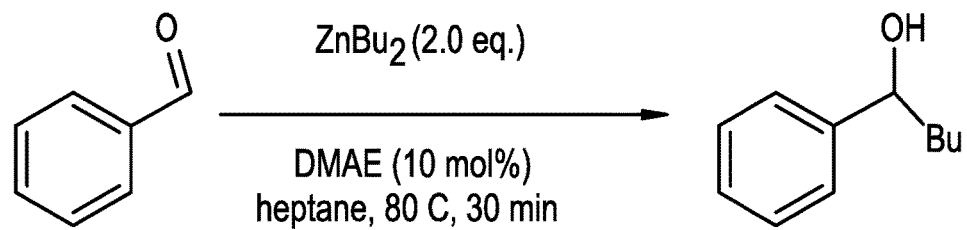
Figure 1C:
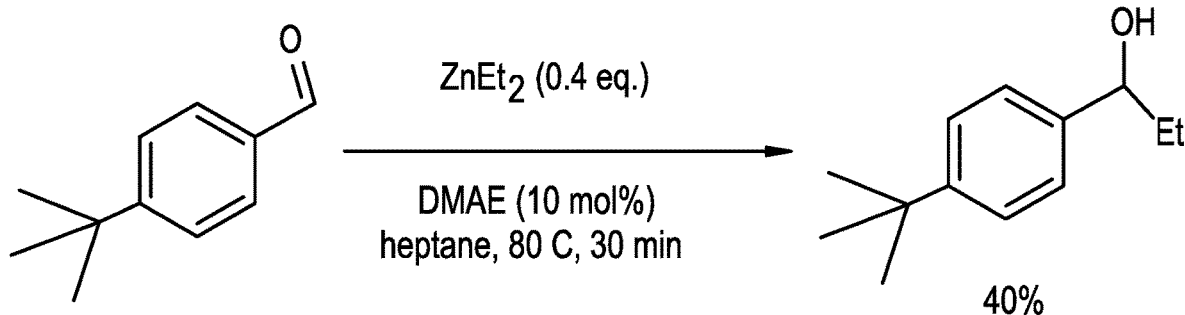
Figure 2:
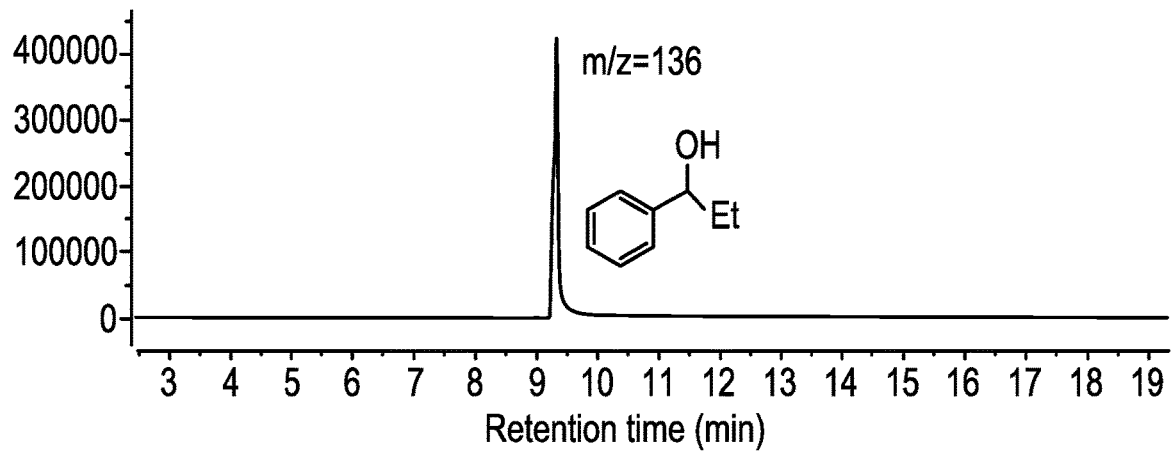
FIG. 2 provides the GCMS scan of the reaction product of benzaldehyde with $ZnEt_2$ at 1:2 molar ratio in the presence of DMAE.
Figure 3:
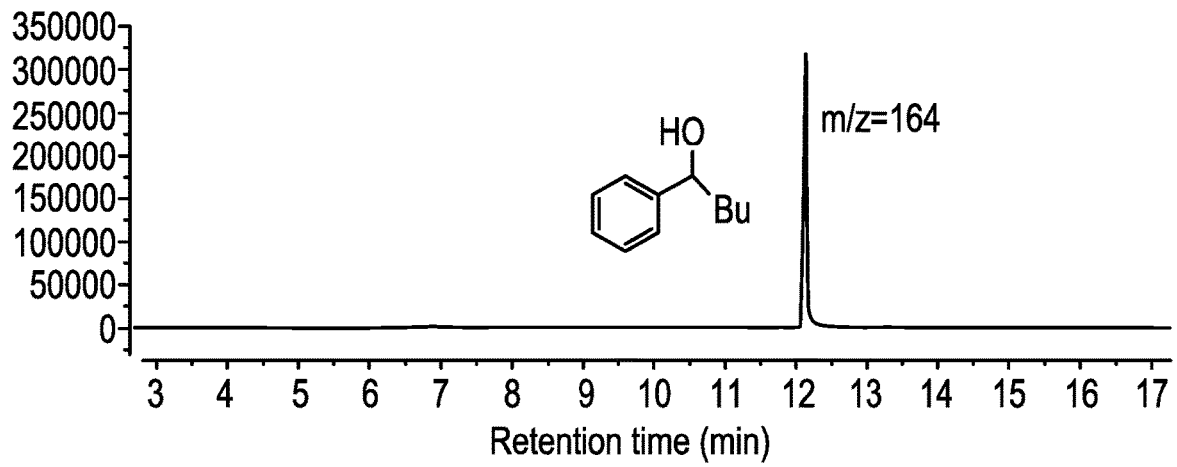
FIG. 3 provides the GCMS scan of the reaction product of benzaldehyde with $ZnBu_2$ with 10 mol % DMAE.
Figure 4:
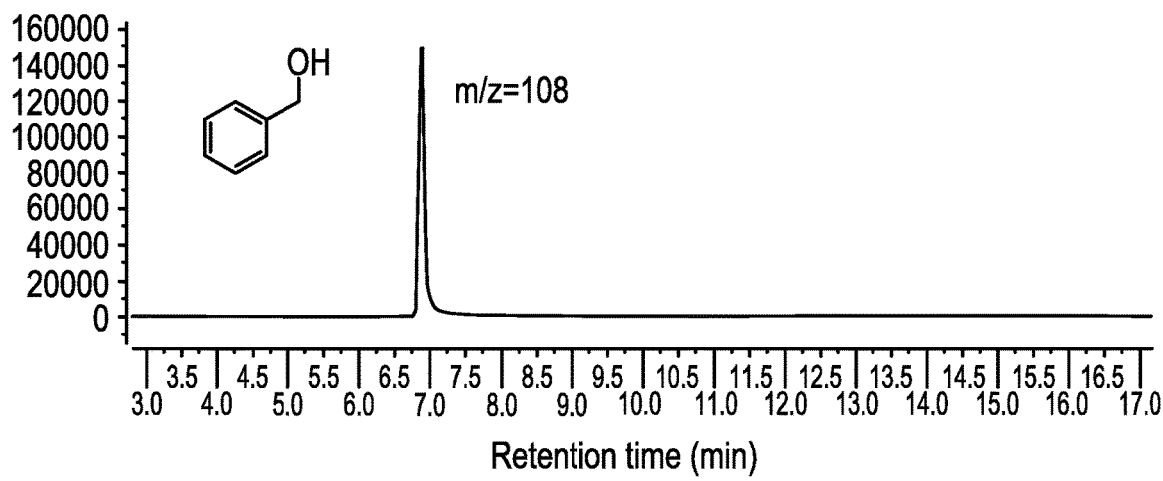
FIG. 4 provides the GCMS scan of the reaction product of benzaldehyde with $ZnBu_2$ at 1:2 molar ratio with no promoter.

In the first set of experiments (FIG. 1, reaction (1)), benzaldehyde and diethyl-zinc were used as the model compounds. GCMS analysis showed that the benzaldehyde was cleanly converted to the addition product without the undesired reductive elimination reaction, as shown in FIG. 2. In the second set of experiments (FIG. 1, reaction (2)), diethyl-zinc was replaced by dibutyl-zinc to investigate if a longer alkyl chain would lead to the undesired reductive elimination reaction. In this regard, as seen in FIG. 3, it was observed that the benzaldyhde was also cleanly converted to the addition product via the addition of dibutyl-zinc. In addition, a control experiment without any promoter was run as comparison. As shown in FIG. 4, no addition product was formed in the control run without promoter, and all starting aldehyde was reduced to benzyl alcohol. Accordingly, in reactions facilitated by DMAE promoter, the clean addition product was obtained and, encouragingly, the reductive elimination reaction product, benzyl alcohol, was not detected.

Figure 5:
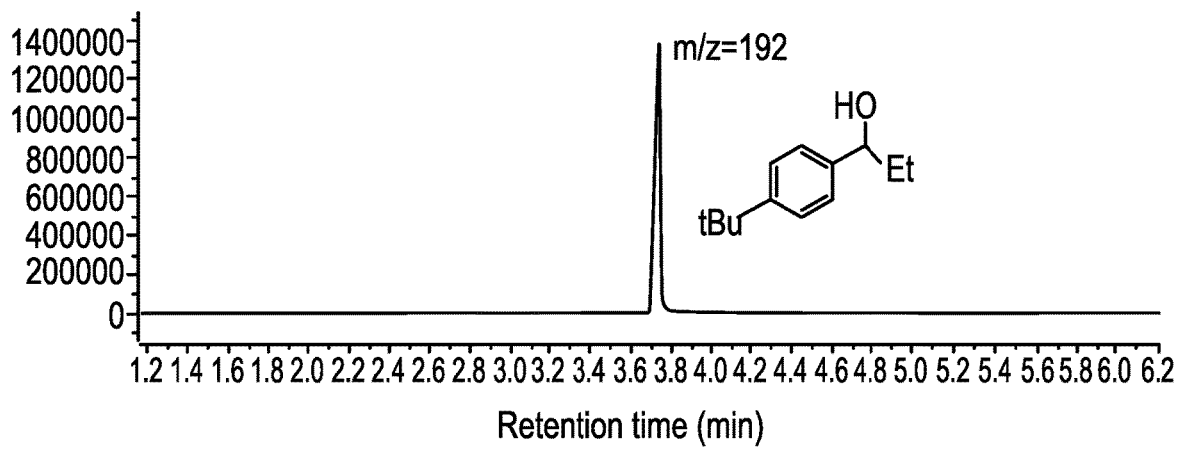
FIG. 5 provides the GCMS scan of the reaction product of tBu-benzaldehyde with $ZnEt_2$ at a tBu-benzaldehyde:$ZnEt_2$ ratio of 1:1.67.
Figure 6:
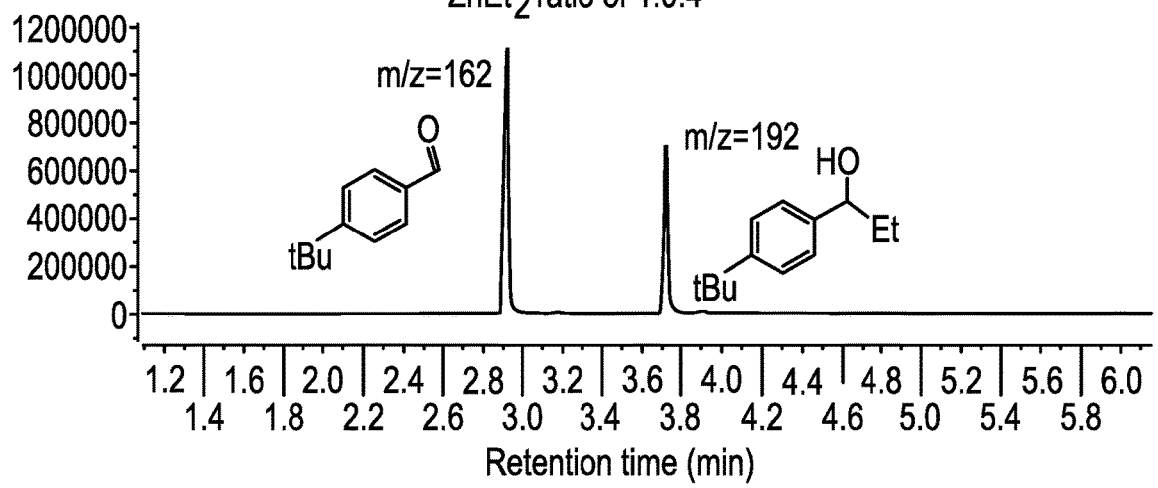
FIG. 6 provides the GCMS scan of the reaction products of tBu-benzaldehyde with $ZnEt_2$ at a tBu-benzaldehyde:$ZnEt_2$ ratio of 1:0.4.

In the two sets of experiments, excess dialkyl-zinc was used. To probe if both alkyl groups on zinc were involved in the reaction, subsequent experiments were carried out using t-butylbenzaldehyde and diethyl-zinc as model compounds at an aldehyde/Zn ratio of 1:1.67 and 1:0.4. In the latter case (at a 1:0.4 molar ratio), an 80% conversion of the starting aldehyde would be expected if both alkyl groups were reacted. As shown in FIG. 5, at an aldehyde/Zn ratio of 1.67, not surprisingly, the aldehyde was completely converted to the addition product. As shown in FIG. 1, reaction (3), and FIG. 6, at an aldehyde/Zn ratio of 0.4, about 40% of aldehyde was converted to the addition product. These results suggested that only one alkyl group on $ZnR'_2$ reacted. This finding was disappointing but not surprising, as the replacement of the first alkyl by an alkoxy group would expectedly make the remaining alkyl less reactive as a nucleophile. In addition, the formation of dimmers, trimers and tetramers as known in literature (e.g., Lewinski et al., *Angew. Chem. Int. Ed.,* 2010, 49, 8266-8269) may further reduce the reactivity.

Accordingly, with the understanding that only one of the two alkyl groups from dialkyl-zinc can be added to an aldehyde in the presence of a β-amino-alcohol promoter, attention was turned to potential Lewis acid promoters as described in the examples below with the hope that a suitable Lewis acid might activate the aldehydes enough to enable the reaction of the second, less reactive alkyl group on zinc metal.

EXAMPLES

Test Methods

Gas Chromatograph-Mass Spectroscopy (GCMS):

Tandem gas chromatography/low resolution mass spectroscopy using electron impact inonization (EI) was performed at 70 eV on an Agilent Technologies 6890N series gas chromatograph equipped with an Agilent Technologies 5975 inert XL mass selective detector and an Agilent Technologies Capillary column (HP1MS, 15 m×0.25 mm, 0.25 micron). Aliquots of CSAs of the present disclosure were quenched with water and analyzed by GCMS using the method described below:

Method:
50° C. for 0 min
then 25° C./min to 300° C. for 10 min
Run Time 20 min $^1$H Nuclear Magnetic Resonance (NMR):

$^1$H NMR spectra were recorded on a Bruker AV-400 spectrometer at ambient temperature. $^1$H NMR chemical shifts in benzene-d$_6$ were referenced to 7.16 ppm (C$_6$D$_5$H) relative to TMS (0.00 ppm). Samples were prepared by dissolution in benezene-d$_6$.

$^{13}$C Nuclear Magnetic Resonance (NMR):

$^{13}$C NMR spectra of polymers were collected using a Bruker 400 MHz spectrometer equipped with a Bruker Dual DUL high-temperature CryoProbe. The polymer samples were prepared by adding approximately 2.6 g of a 50/50 mixture of tetrachloroethane-d$_2$/orthodichlorobenzene containing 0.025M chromium trisacetylacetonate (relaxation agent) to 0.2 g of polymer in a 10 mm NMR tube. The samples were dissolved and homogenized by heating the tube and its contents to 150° C. The data was acquired using 320 scans per data file, with a 7.3 second pulse repetition delay with a sample temperature of 120° C.

Materials and Preparation

Unless otherwise noted, all chemical reagents are used as received ZnEt$_2$ is obtained from Akzo Nobel ZnBu$_2$ is obtained from Fisher Scientific. Benzaldehyde, t-butylbenzaldehyde, dimethylaminoethanol, MgCl$_2$, MgBr$_2$.OEt$_2$, TiCl$_4$, LiBr, ZrCl$_4$, ZnCl$_2$, Ti(OiPr)$_4$, ClTi(OiPr)$_3$ are obtained from Sigma-Aldrich. Solvents are degassed by sparging with dry nitrogen and dried over activated alumina (activated in 275° C. oven for 5 hours) beads prior to use. All experiments are conducted either in a glovebox or Schlenk line under a nitrogen atmosphere.

Synthesis of Bis(dimethylamido)dichlorotitanium ((NMe$_2$)$_2$TiCl$_2$): Ti(NMe$_2$)$_4$ (4 g, 17.8 mmol) is dissolved in 70 ml of toluene and cooled in a freezer. TiCl$_4$ (3.385 g, 17.8 mmol) in 4 ml of toluene is slowly added. The reaction mixture is stirred at room temperature overnight and then filtered (red solution). The filtrate is concentrated to give a brown powder which is washed with pentane and dried in vacuum. 6.98 g of brown powder is obtained. Yield: 94.5%.

$^1$H NMR (400 MHz, benzene-d6, 298 K): δ=2.96 (s, 12H, CH$_3$).

Addition of Alkyl-Zinc to Aldehydes in the Presence of a Lewis Acid

As shown in Table 1 below, nine Lewis acids are evaluated for functionalizing alkyl-zinc via addition of alkyl-zinc to aldehydes in existing solution processes. As seen in Table 1, seven resultant compounds (i.e., GCMS products) are identified. In Table 1, the time column indicates the time at which aliquots are taken for GCMS analysis. In this regard, it is understood that the reaction times for arriving at the GCMS products is equal to or less than the times indicated under the time column.

The reactions are carried out in 4 oz glass vials equipped with a stir bar, septum cap, and connected to Schlenk line via a needle. In a typical experiment, dialkyl-zinc (1.5 mmol) is dissolved in 5 ml solvent (toluene or octane) and heated to the desired reaction temperature. Lewis acid (1.5 mmol or prescribed amount) and aldehyde (3.0 mmol) are separately injected by syringe through the septum to start the reaction. Alternatively, dialkyl-zinc, Lewis acid and aldehyde are premixed in the vial in the drybox, then immediately taken out of the drybox, connected to Schlenk line, and placed on a heating plate. Aliquots are taken periodically, hydrolyzed by water, and analyzed by GCMS.

In most cases, the functionalized compounds are not isolated due to difficulty to separate the mixture, with a few exceptions such as compound 6 and compound 7, which are isolated and analyzed by NMR. In most of the experiments, the aldehyde/ZnR'$_2$ is kept at the stoichiometric ratio of 1:0.5 so the conversion of the aldehyde is correlated to the conversion of ZnR'$_2$. A >50% conversion of aldehyde would indicate the reaction of at least some of the second R' group.

TABLE 1

Screen of Lewis acids

| Entry | ZnR'2 | Catalyst | Ald*/Zn/Cat | Temp, ° C. | Time, min | GCMS Product** | | | | | | | Prod yield*** |
| | | | | | | 1 | 2 | 3 | 4 | 5 | 6 | 7 | |
|---|---|---|---|---|---|---|---|---|---|---|---|---|---|
| 1 | ZnEt2 | MgCl2 | 1/0.5/1 | 80 | 30 | 73.4 | 4.3 | 24.2 | 2.6 | | | | 27 |
| 2 | ZnEt2 | MgBr2.OEt2 | 1/0.5/0.5 | 80 | 30 | trace | 20.4 | 52.8 | 26.8 | | | | 75 |
| 3 | ZnEt2 | MgBr2.OEt2 | 1/0.5/0.05 | 80 | 30 | 57.1 | 4.1 | 34 | 4.7 | | | | 39 |
| 4 | ZnEt2 | MgBr2.OEt2 | 1/0.5/0.1 | 80 | 30 | 6.4 | 27.3 | 22.6 | 43.7 | | | | 66 |
| 5 | ZnEt2 | LiBr | 1/0.5/0.1 | 80 | 30 | 39.1 | 6.6 | 46.4 | 7.8 | | | | 54 |
| 6 | ZnEt2 | TiCl4 | 1/0.5/0.5 | 110 | 10 | complex unknown peaks | | | | | | | |
| 7 | ZnEt2 | ZrCl4 | 1/0.5/0.5 | 110 | 10 | trace | 35.2 | trace | 52.8 | 12 | | | 53 |
| 8 | ZnEt2 | ZrCl4 | 1/0.5/0.5 | 110 | 30 | trace | 38.5 | trace | 38.5 | 23 | | | 50 |
| 9 | ZnEt2 | (NMe2)2TiCl2 | 1/0.5/0.5 | 110 | 10 | | | | | | ~100 | | ~100 |
| 10 | ZnEt2 | ZnCl2 | 1/0.5/0.5 | 110 | 10 | 27.1 | 12.7 | 43.1 | 17 | | | | 60 |
| 11 | ZnEt2 | (NMe2)2TiCl2 | 1/0.5/0.5 | 110 | 30 | | | | | | ~100 | | ~100 |
| 12 | ZnEt2 | ZnCl2 | 1/0.5/0.5 | 110 | 30 | 14.2 | 18 | 47 | 20.7 | trace | | | 68 |
| 13 | ZnEt2 | Ti(OiPr)4 | 1/0.5/0.1 | 110 | 10 | 45.8 | trace | 54.2 | trace | | | | 54 |
| 14 | ZnEt2 | Ti(OiPr)4 | 1/0.5/0.1 | 110 | 30 | 40 | 4 | 51.2 | 8.6 | | | | 60 |
| 15 | ZnEt2 | Ti(OiPr)4 | 1/0.5/0.1 | 110 | 60 | 32.5 | 7.8 | 44.8 | 14.9 | | | | 60 |
| 16 | ZnEt2 | Ti(OiPr)4 | 1/0.5/0.5 | 80 | 30 | 41 | 59 | | | | | | 59 |
| 17 | ZnEt2 | Ti(OiPr)4 | 1/0.5/0.5 | 80 | 60 | 40 | 60 | | | | | | 60 |
| 18 | HexOZnEt | (NMe2)2TiCl2 | 1/2/0.5 | 80 | 30 | | | | | | ~100 | | ~100 |
| 19 | Zn"Bu2 | (NMe2)2TiCl2 | 1/0.5/0.5 | 80 | 10 | trace | | | | | | ~100 | ~100 |
| 20 | Zn"Bu2 | ClTi(OiPr)3 | 1/0.5/0.5 | 80 | 10 | multiple unknown peaks | | | | | | | |

Figure 7:
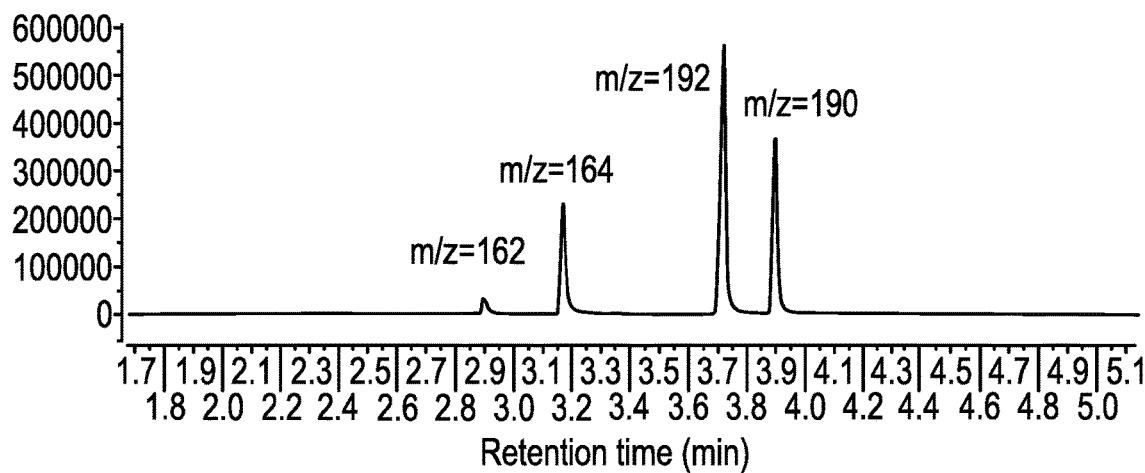
FIG. 7 provides the GCMS scans and structures of compounds 1-4 in connection with Table 1.
Figure 7:
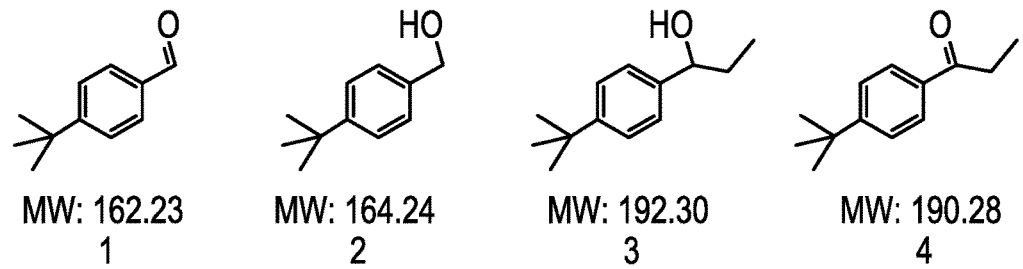
Figure 8:
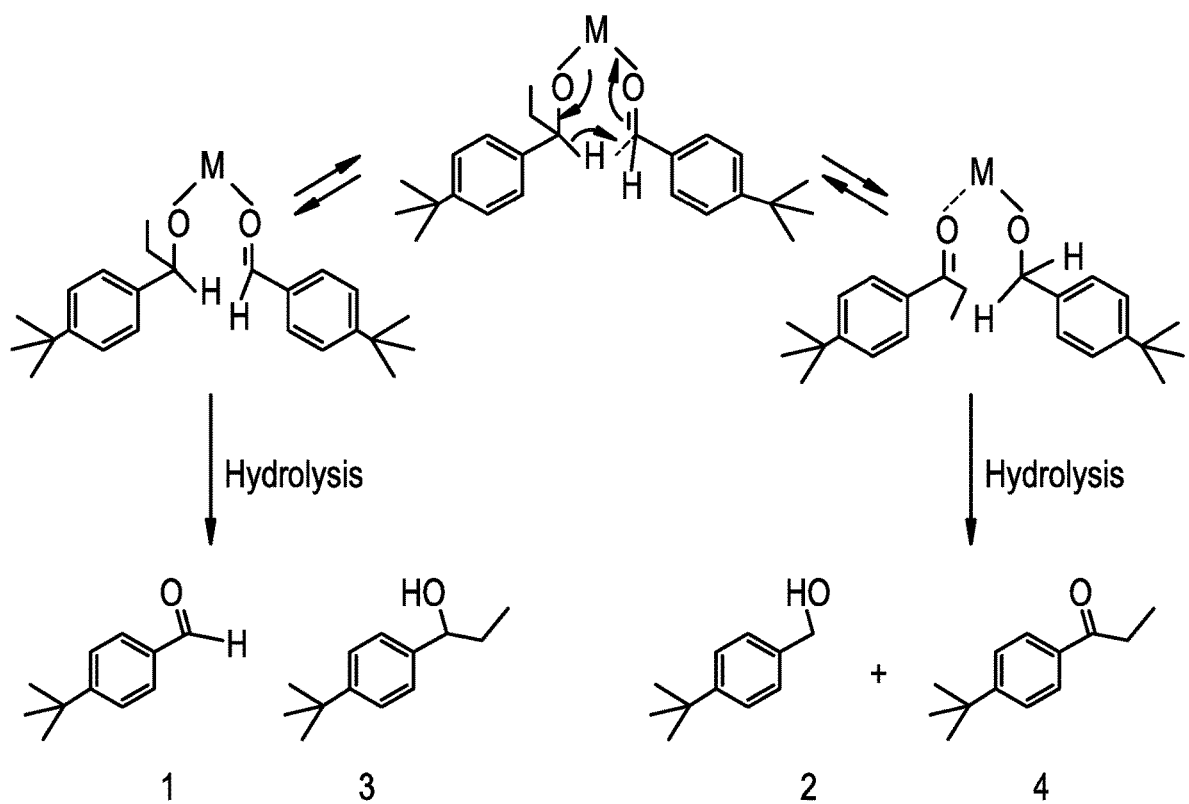
FIG. 8 provides possible Meerwein-Ponndorf-Verley (MPV) reduction reactions for compounds 2 and 4 in connection with Table 1.
Figure 9:
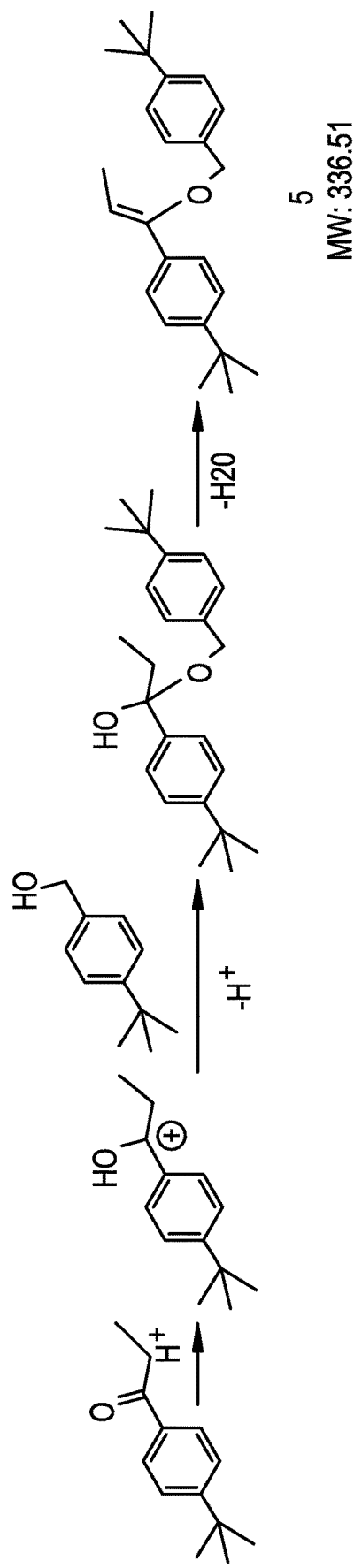
FIG. 9 provides a possible pathway for forming compound 5 in connection with Table 1.

*Ald = p-tBubenzaldehyde;
**The yields are rough estimation from peak integration without calibration;
***Sum of addition products 3 to 7;
"Catalyst" here refers to the promoter In most reactions shown in Table 1, four GCMS products (compounds 1-4) are observed. A typical GCMS scan and the four corresponding compounds are shown in FIG. 7. Compound 1 is the starting aldehyde, and compound 3 is the expected addition product. The primary alcohol, compound 2, may have been generated through Meerwein-Ponndorf-Verley (MPV) reduction as shown in FIG. 8. As seen in FIG. 8, the MPV reduction would generate compound 4 at the same time. However, it is also possible that some of compound 4 is generated due to oxidation during hydrolysis. As seen in Table 1, in a few cases, an unknown species, compound 5, with m/z=336 is observed. It is suspected to be a product formed during hydrolysis due to the acidic medium, as shown in FIG. 9; however, no attempt was made to confirm the structure.

As seen in Table 1, most Lewis acids evaluated, with the exception of bis(dimethylamido)dichlorotitanium (i.e., $(NMe_2)_2TiCl_2$), results in mixtures of products. It was encouraging that several runs with these Lewis acids show greater than 50% conversion to the addition products, indicating that at least some of the second alkyl group reacted. For example, 75% conversion is obtained with $MgBr_2 \cdot OEt_2$ (Entry 2).

Figure 10A:
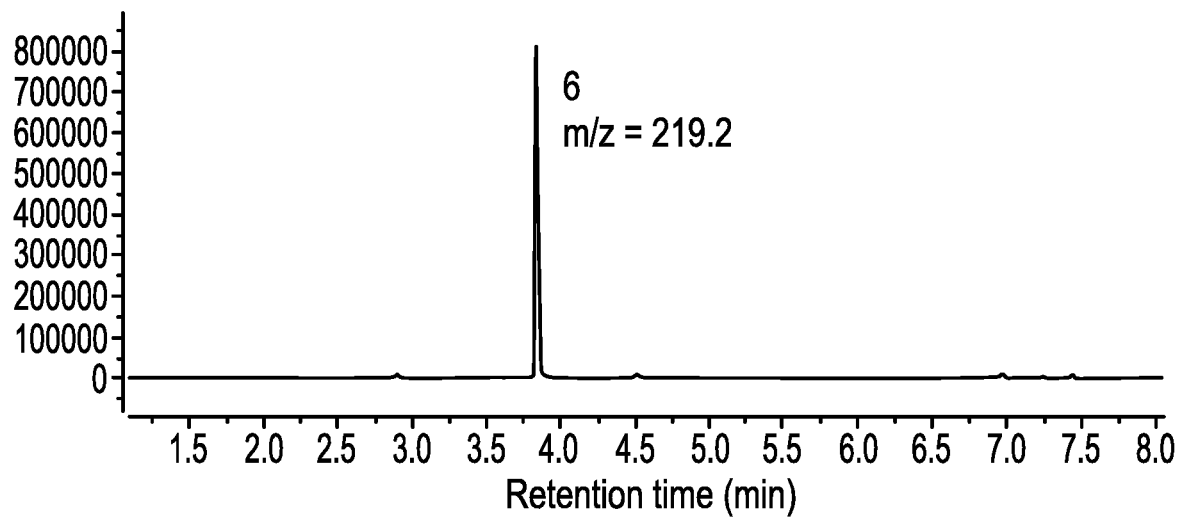
FIG. 10 provides the GCMS scans of compounds 6 and 7 in connection with Table 1.
Figure 10B:
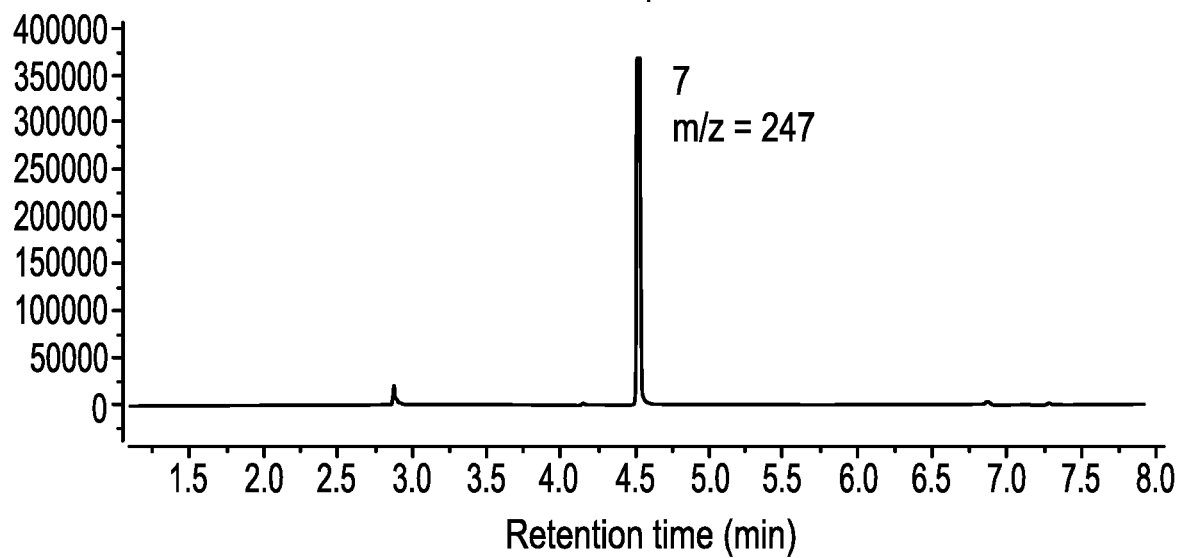
Figure 11:
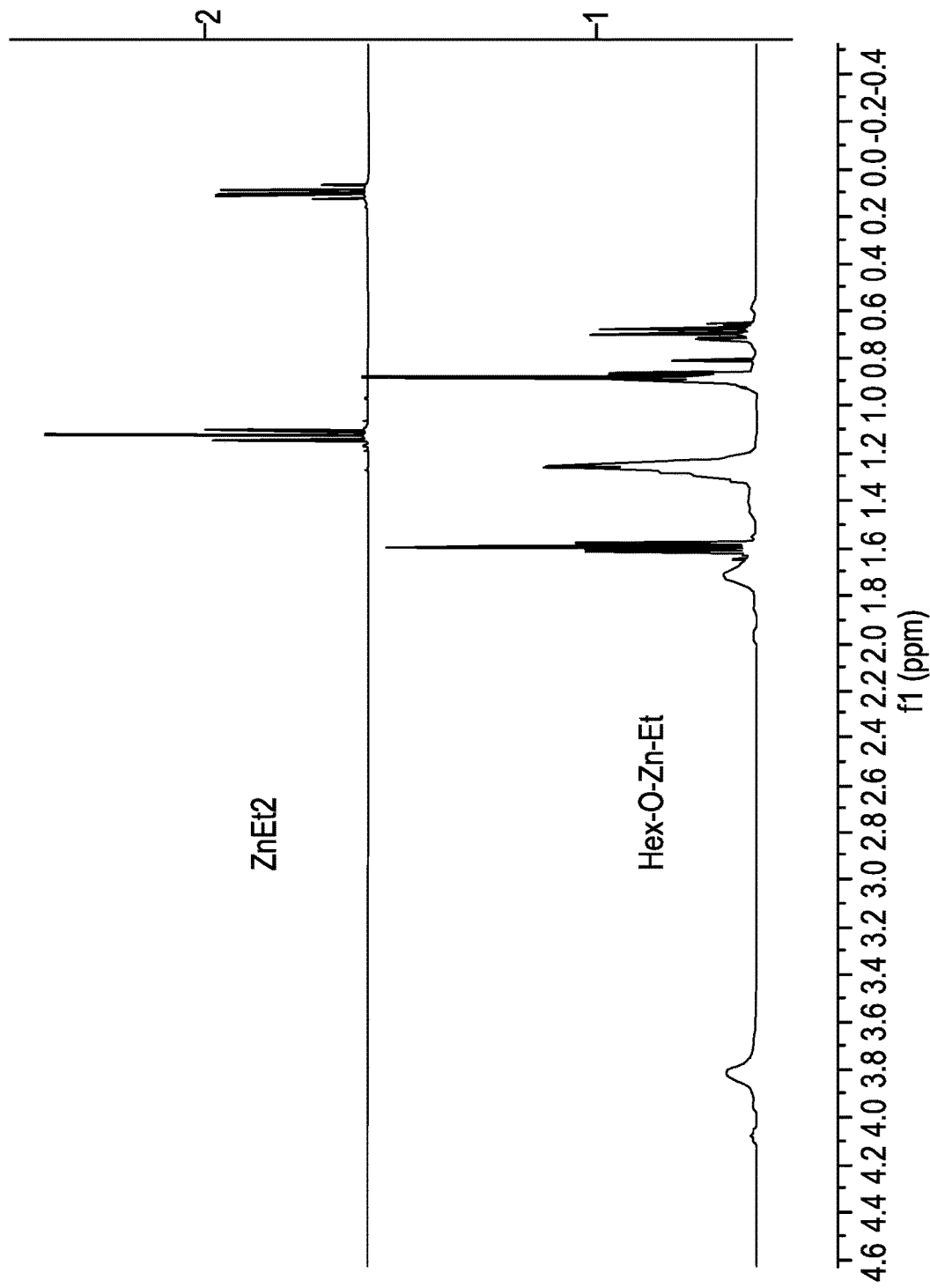
FIG. 11 provides the $^1H$ NMR spectrum of Hexyloxyethylzinc.

The most surprising and unexpected result is obtained when $(NMe_2)_2TiCl_2$ is used as promoter (Entry 9). Within 10 minutes, the starting aldehyde is converted to compound 6, shown as a clean peak with m/z value of 219 on GCMS (FIG. 10). The molecular weight of the product is not consistent with that of any anticipated products. The complete disappearance of the starting aldehyde indicates the conversion of both ethyl groups on zinc. In a subsequent reaction, diethyl-zinc is replaced by dibutyl-zinc (Entry 19). This time, another clean product, compound 7, is obtained with m/z of 247 (FIG. 10). The difference in molecular weight between compounds 6 and 7 is consistent to that between ethyl and n-butyl groups, suggesting that they are addition products. In the reaction with dibutyl-zinc, a small amount of starting aldehyde is visible on GCMS, which is likely attributable to inaccurate dosage of dibutyl-zinc (the concentration of the solution might be less than the value on the label due to partial decomposition as evidenced by grey precipitation). To further verify that the second R' group was reactive, a reaction is conducted using a monoalkyl zinc alkoxide compound (Entry 18). FIG. 11 shows the $^1H$ NMR of hexyloxyethylzinc prepared by mixing diethylzinc with hexanol at 1:1 ratio in $C_6D_6$ at room temperature. In this reaction with the monoalkyl zinc alkoxide, the product with molecular weight of 219 is cleanly obtained, proving that the second alkyl is reactive after the first alkyl was replaced by the alkoxy group.

Functionalization of Alkyl-Zinc

Figure 12A:
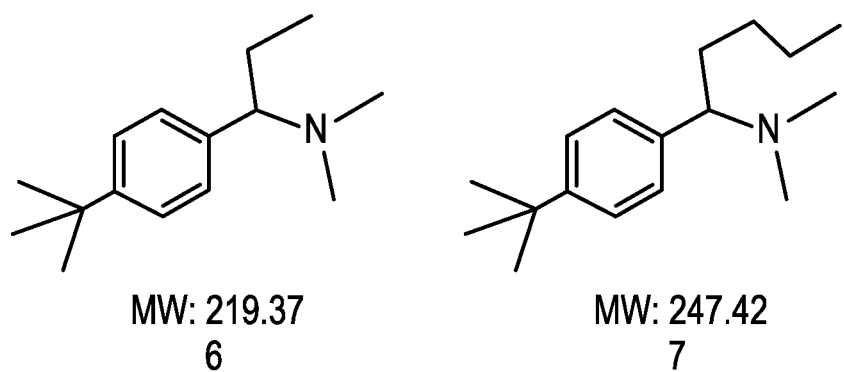
FIG. 12 provides the $^1H$ NMR spectra of compounds 6 and 7 in connection with Table 1.
Figure 12B:
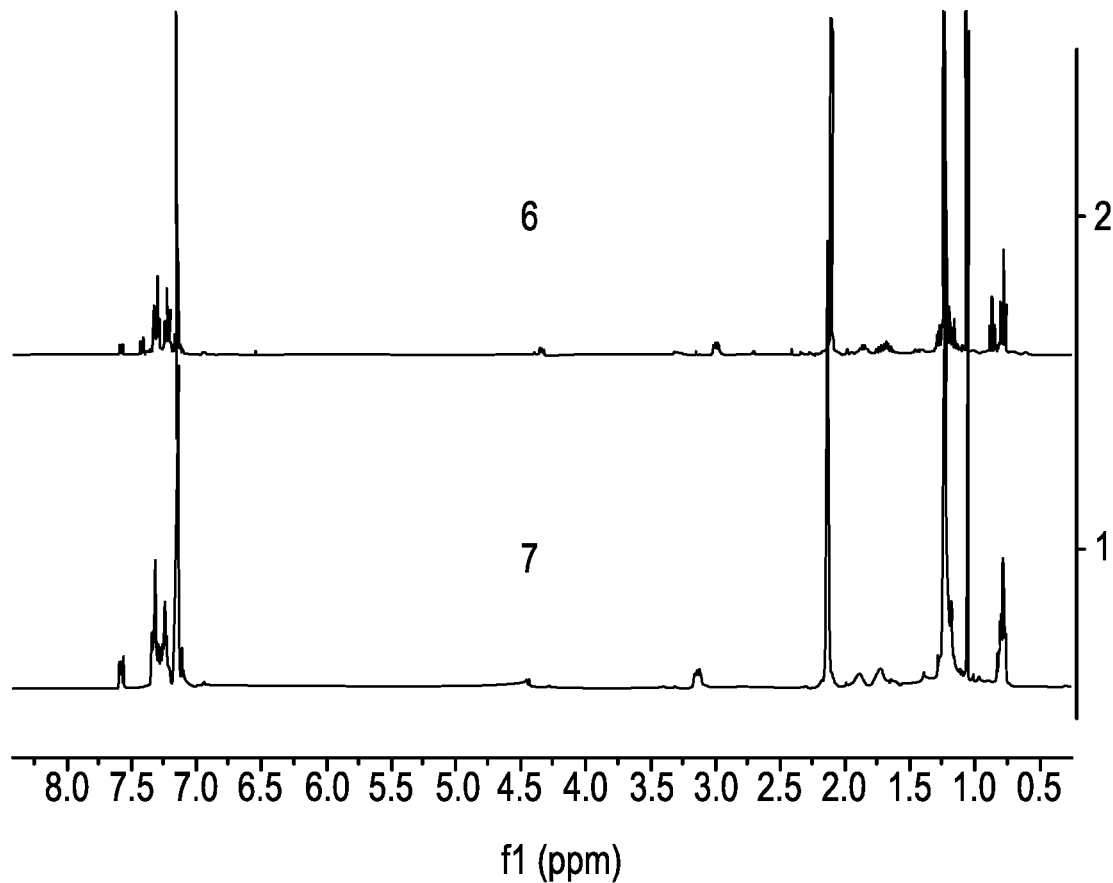
Figure 13:
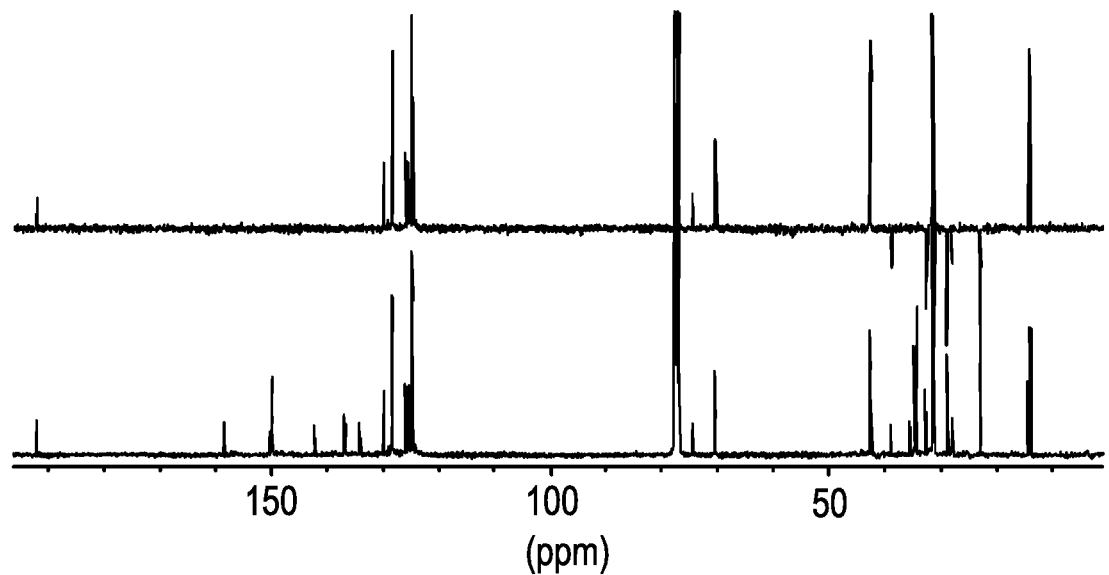
FIG. 13 provides the $^{13}C$ NMR spectrum of compound 7 in connection with Table 1.

As discussed above, the present inventors surprisingly and unexpectedly discovered that the simple, one-pot reaction shown below results in functionalization of alkyl-zinc (e.g., compounds 6 and 7 with amino functional groups). Compounds 6 and 7 are portrayed in FIG. 12, along with their $^1H$ NMR spectra. The $^{13}C$ NMR spectra for compound 7 is also provided in FIG. 13.

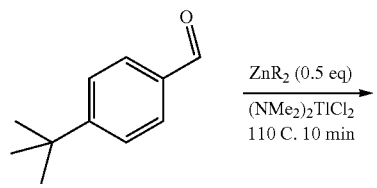

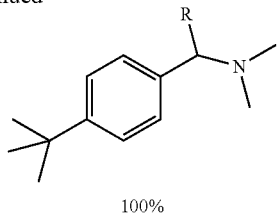

100%

The proposed reaction mechanism is shown below, where the carbonyl oxygen of the aldehyde is geminally substituted by an amino group from titanium and an alkyl group from zinc.

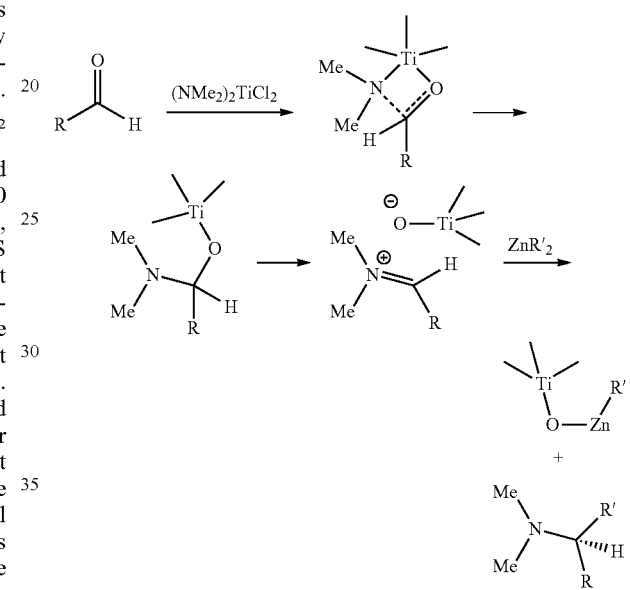

Accordingly, with the addition of alkyl-zinc to aldehydes in the presence of $(NMe_2)_2TiCl_2$, the present inventors have surprisingly and unexpectedly discovered a simple, one-pot reaction for synthesizing functional polymers that is adaptable to existing solution processes. In other words, this simple, one-pot reaction demonstrates the transfer of alkyl groups to the aldehyde without the undesired reductive elimination reaction, is facile at high temperatures (e.g., 110° C.), can be completed in a reasonably short amount of time (e.g., within 10 minutes), and exhibits the reaction of both R' groups of $ZnR'_2$.

This simple, one-pot reaction of the present disclosure is not limited to the use of the promoter bis(dimethylamido)dichlorotitanium (i.e., $(NMe_2)_2TiCl_2$). As a person of ordinary skill in the art would understand after review of the present disclosure, Lewis acids with formulas similar to that of bis(dimethylamido)dichlorotitanium can be utilized in the present simple, one-pot reaction. Accordingly, as a person of ordinary skill in the art would understand upon review of the present disclosure, the promoter that can be used in the simple, one-pot reaction of the present disclosure has the formula $(R_2N)_nMX_{4-n}$, wherein n is an integer from 1-3; X is Cl, Br, or I; R is a $C_{1-10}$ hydrocarbon; and M is a Group 4 metal.

Figure 14:
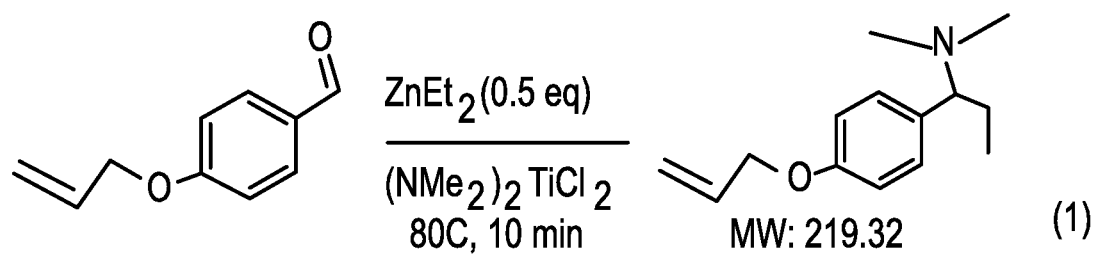
FIG. 14 portrays exemplary reactions for inclusion of different functional groups on an alkyl chain.
Figure 14:
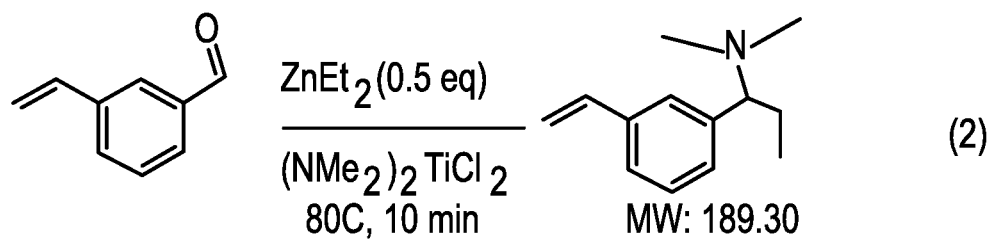
Figure 15A:
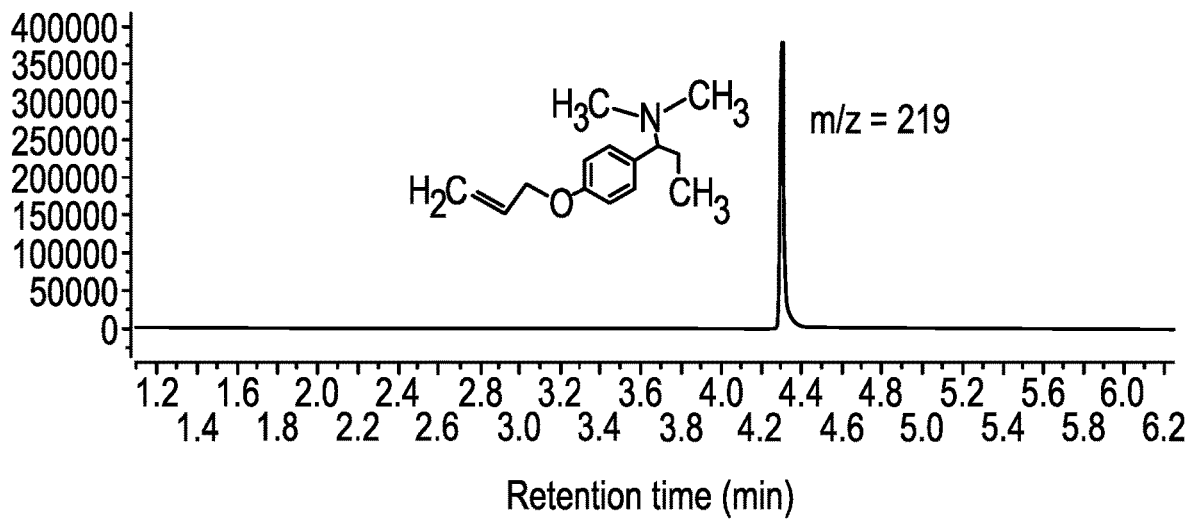
FIG. 15 provides the GCMS scans for allyloxy and vinyl containing products.
Figure 15B:
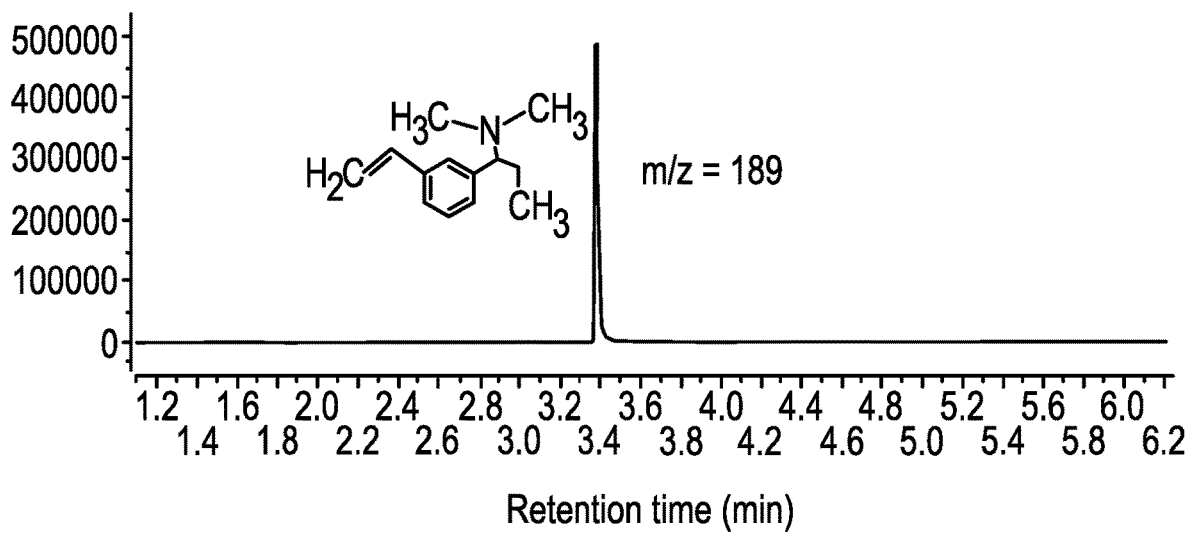
Figure 16A:
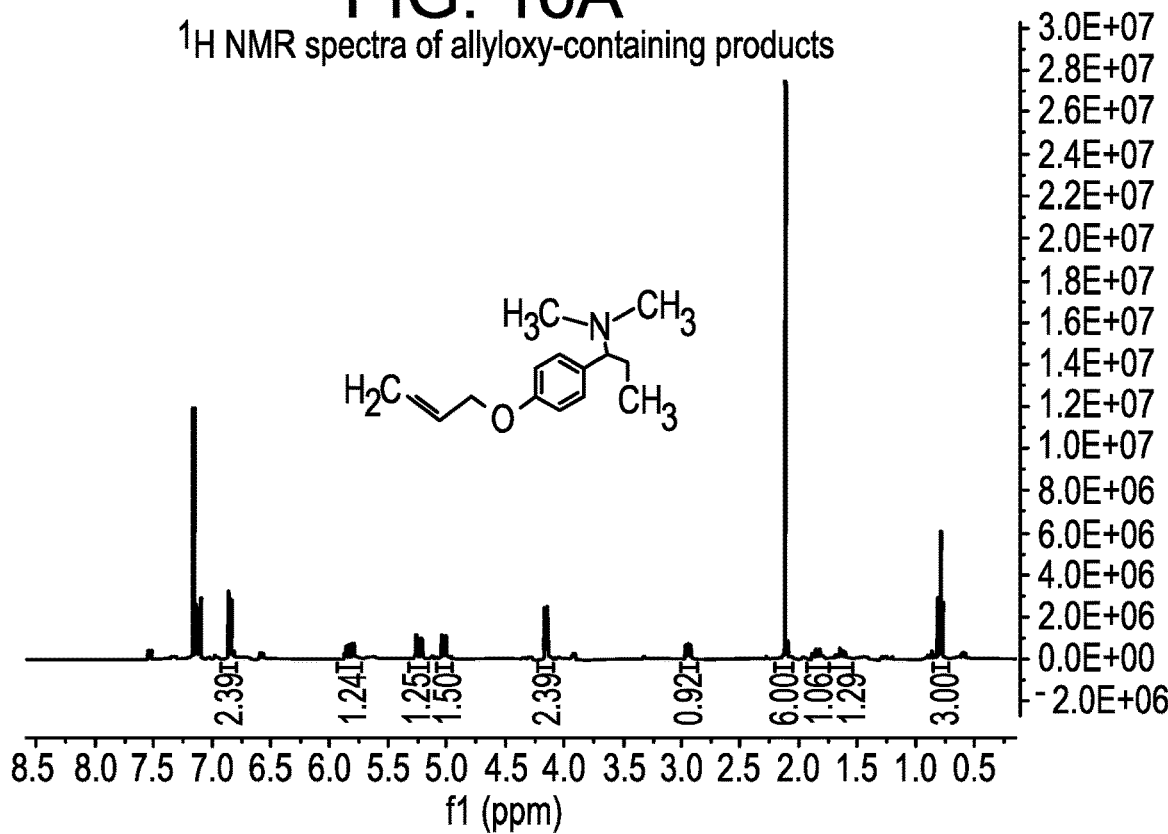
FIG. 16 provides the $^1H$ NMR spectra for allyloxy and vinyl containing products.
Figure 16B:
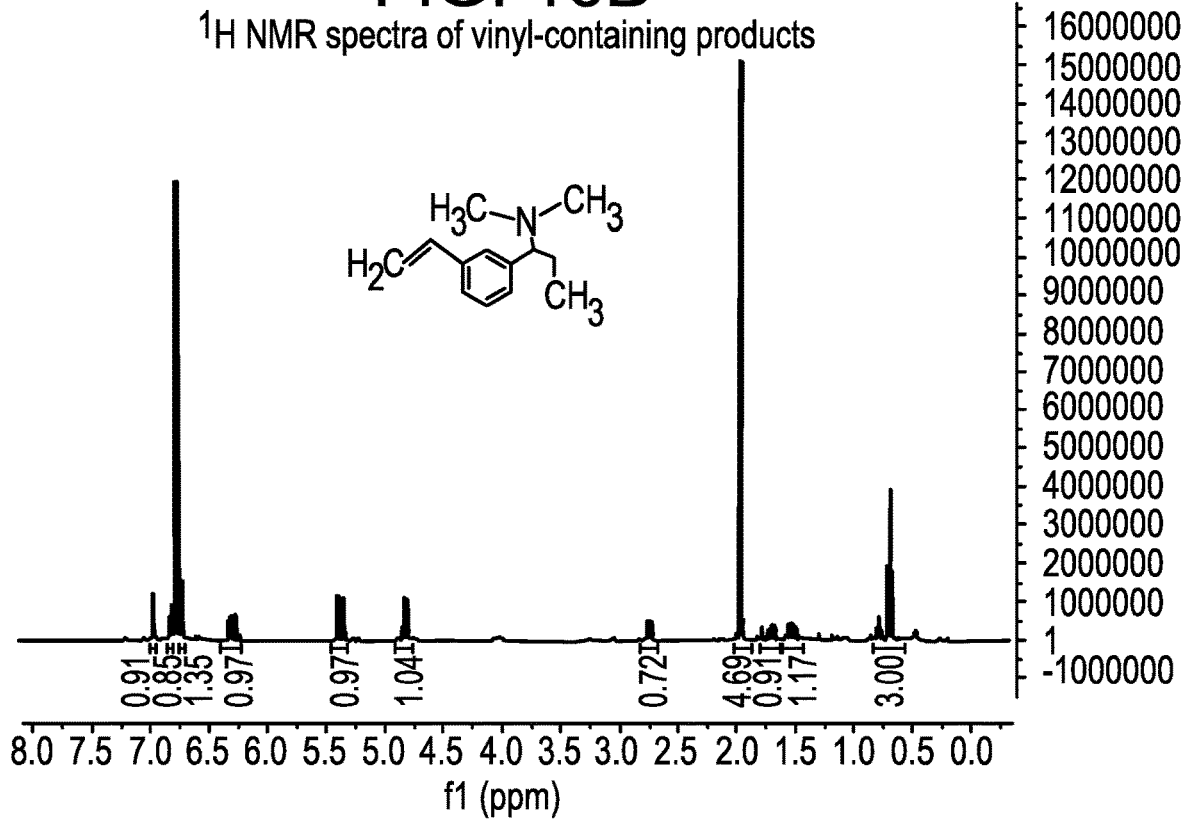

Further, this simple, one-pot reaction of the present disclosure is not limited to functionalization by addition of amino groups from $(R_2N)_nMX_{4-n}$. For example, other functional groups may be added to the alkyl chain via inclusion of the functional groups on the aldehyde. To demonstrate the utility of this chemistry to add other functional groups to alkyl chains, two benzaldehydes, one bearing an allyloxy group and the other bearing a vinyl group, are reacted with 0.5 eq of ZnEt$_2$ in the presence of 0.5 eq of (NMe$_2$)$_2$TiCl$_2$ in toluene at 80° C. Such reactions are portrayed in FIG. 14, reactions (1) and (2), respectively. Both reactions are quenched at 10 min. and GCMS showed complete conversion of starting aldehydes to clean polymer products, one bearing an amino group and an allyloxy group and the other bearing an amino group and a vinyl group (FIG. 15). The $^1$H NMR of the crude products after brief workup provides support for the structures (FIG. 16). The following information is provided in connection with FIG. 16: Compound 6: $^1$H NMR (400 MHz, C$_6$D$_6$) δ 7.30 (m, aromatic CH), δ 7.23 (m, aromatic CH), δ 2.99 (m, CH), δ 2.11 (s, N(CH$_3$)$_2$), δ 1.6-1.9 (m, CH$_2$CH$_3$), δ 1.23 (s, C(CH$_3$)$_3$), δ 0.7-0.9 (t, CH$_2$CH$_3$); Compound 7: $^1$H NMR (400 MHz, C$_6$D$_6$) δ 7.31 (m, aromatic CH), δ 7.25 (m, aromatic CH), δ 3.15 (m, CHN), δ 2.14 (s, N(CH$_3$)$_2$), δ 1.64-1.96 (m, CH$_2$CH$_2$CH$_2$CH$_3$), δ 1.24 (s, C(CH$_3$)$_3$), δ 1.11-1.25 (m, CH$_2$CH$_2$CH$_2$CH$_3$), δ 0.78 (m, CH$_2$CH$_3$). $^{13}$C NMR (400 MHz, C$_6$D$_6$) δ 149.76 (aromatic CH); δ 136.85 (aromatic CH); δ 128.34 (aromatic CH); δ 124.83 (aromatic CH); δ 70.35 (CHN); δ 42.62 (N(CH$_3$)$_2$); δ 34.45 (C(CH$_3$)$_3$); δ 32.68 (CH$_2$CH$_2$CH$_2$CH$_3$); δ 31.44 (C(CH$_3$)$_3$) δ 28.79 (CH$_2$CH$_2$CH$_2$CH$_3$); δ 22.85 (CH$_2$CH$_2$CH$_2$CH$_3$); δ 14.06 (CH$_2$CH$_3$)

Accordingly, in certain embodiments of the present disclosure, the simple, one-pot reaction of the present disclosure can be utilized to add other functional groups to alkyl/polymer chains, such as vinyl, allyloxy, and styryl groups.

Functionalization of Polymeryl-Zinc

In addition to the functionalization of alkyl-zinc, the present inventors confirmed that the simple, one-pot reaction of the present disclosure can be utilized to functionalize polymeryl-zinc by employing polymeryl zinc and aldehyde in the presence of a Lewis acid with the formula (R$_2$N)$_n$MX$_{4-n}$, wherein the polymeryl zinc may be formed via chain shuttling and coordinative chain transfer polymerization technologies, as demonstrated by the examples below and portrayed in the exemplary, non-limiting reaction shown below (where PO refers to polyoctene).

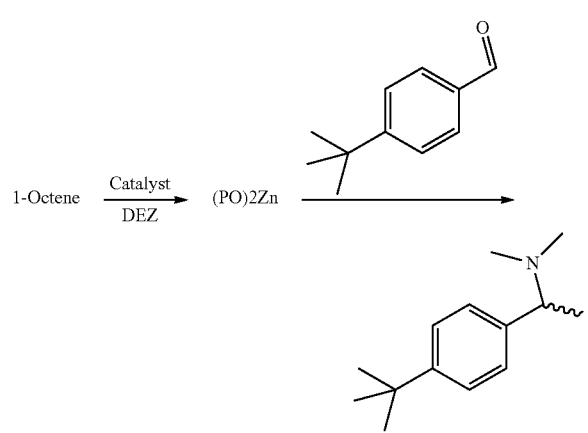

Accordingly, in certain embodiments, the present disclosure relates to a facile, one-pot reaction for synthesizing functional polymers by employing polymeryl-zinc and aldehyde in the presence of a promoter with the formula (R$_2$N)$_n$MX$_{4-n}$, wherein the polymeryl-zinc is a polymer composition formed by a polymerization process, the polymerization process comprising: contacting at least one addition polymerizable monomer with a catalyst composition under polymerization conditions, the catalyst composition comprising the contact product of at least one catalyst precursor, at least one co-catalyst, and at least one chain shuttling agent.

As a non-limiting example, the present inventors attempted to functionalize 1-octene homopolymer synthesized in a glass vial in a glove box using (E)-((2,6-diisopropylphenyl)(2-methyl-3-(octylimino)butan-2-yl)amino) trimethyl hafnium catalyst, bis(hydrogenated tallow alkyl) methylammonium tetrakis(pentafluorophenyl) borate activator, and ZnEt$_2$ as chain shuttling agent. 1-octene (11 ml, 70 mmol), bis(hydrogenated tallow alkyl)methylammonium tetrakis(pentafluorophenyl)borate (0.0028 mmol), and diethyl-zinc (1.0 mmol) are added to 40 ml glass vials and put in a heating block at 80° C. in the drybox. (E)-((2,6-diisopropylphenyl)(2-methyl-3-(octylimino)butan-2-yl) amino)trimethyl hafnium catalyst (0.002 mmol) is added to start polymerization. After 30 minutes, (NMe$_2$)$_2$TiCl$_2$ (0.207 g, 1.0 mmol) suspended in octane is added to the polymerization vial followed by tbu-benzaldehyde (2.0 mmol). The reaction is maintained at 80° C. for 30 min, then taken out of the drybox and quenched in excessive amounts of MeOH. The sticky polymer is separated, re-dissolved in toluene, precipitated in MeOH, separated and dried in a vacuum overnight. The polymers are again re-dissolved in toluene and precipitated in IPA to remove any low molecular weight impurities.

Figure 17:
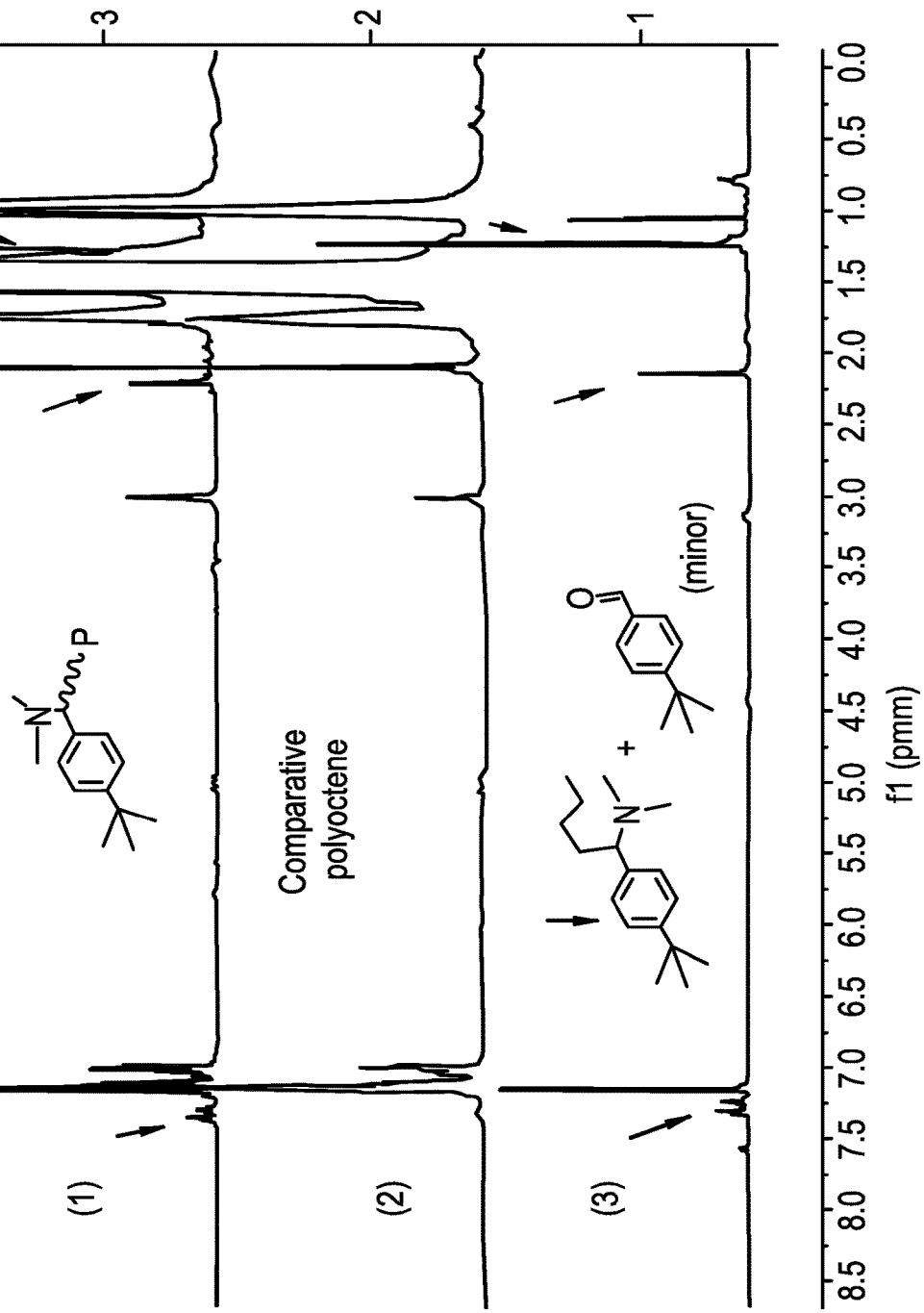
FIGS. 17 and 18 provide the $^1H$ NMR spectra of functionalized polyoctene, comparative polyoctene, and functionalized model compound.
Figure 18:
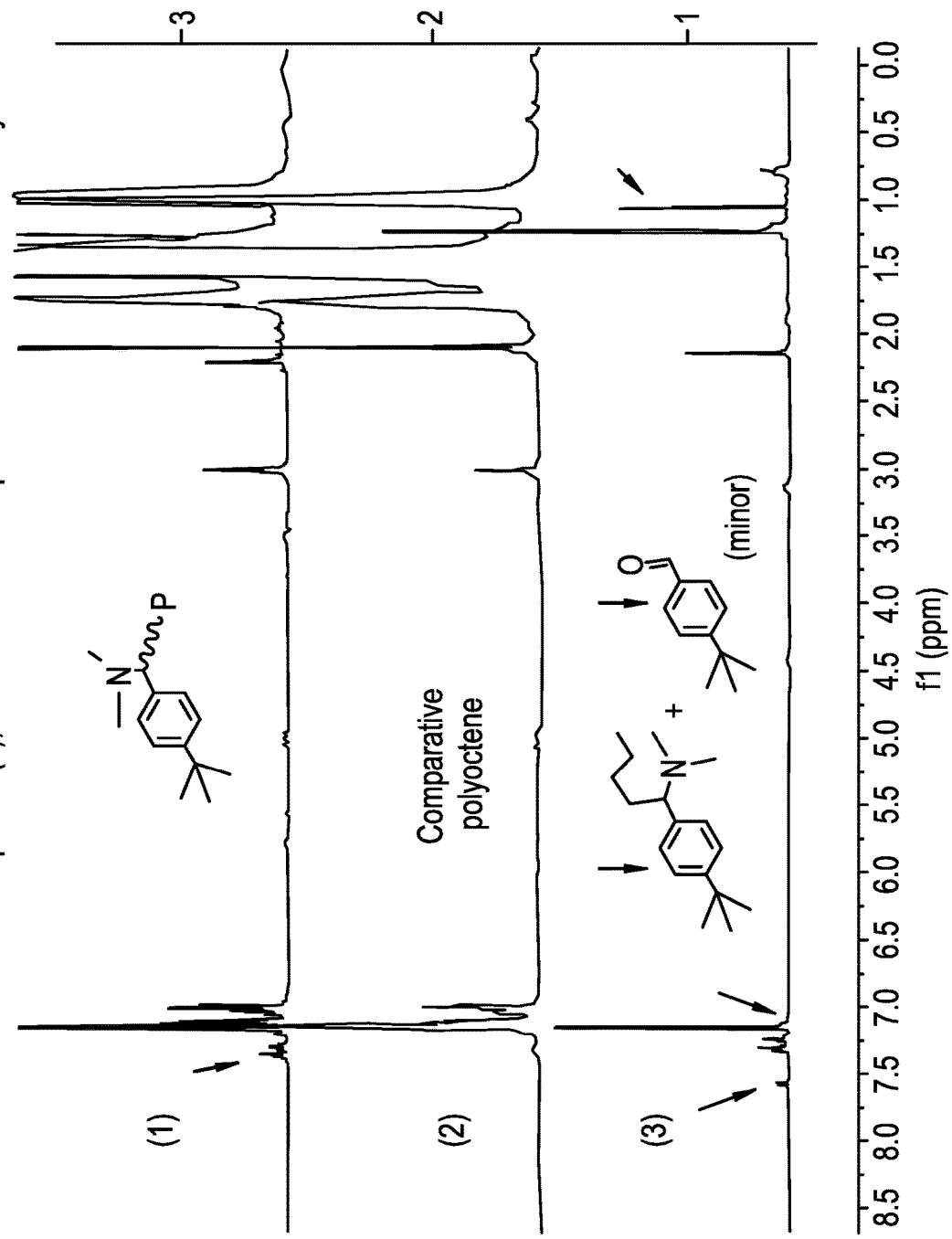

A comparative run is made under the same conditions in the absence of ZnEt$_2$, and, therefore, no functionalized polymer is expected to be made even though the polymer is treated with (NMe$_2$)$_2$TiCl$_2$ and t-butylbenzaldehyde in the same manner. The comparative polymer is worked up using the same procedure to verify that the unreacted functionalization reagents can be totally removed with excess methanol. The $^1$H NMR spectra of the functionalized polyoctene, comparative polyoctene, and a model of the expected compound are compared in FIG. 17, in which the peaks of the functionalized amino group are indicated by the arrows. The peaks of the unreacted aldehyde are indicated by the arrows in the same $^1$H NMR spectra in FIG. 18. These characteristic peaks appear at 1.06 ppm (t-butyl of the aldehyde), 1.23 ppm (t-butyl of the amino product), 2.14 ppm (dimethylamine group), 7.1 and 7.6 ppm (aromatic protons of the aldehyde), and 7.2-7.4 ppm (aromatic protons of the amino product). As can be seen, the comparative polymer does not show any peaks corresponding to functional groups or residual functionalization agents, while the functionalized polymer produced in the presence of ZnEt$_2$ clearly shows the peaks of the functional group consistent with that of the model compound of the expected product.

Accordingly, as seen from NMR characterization, the resulting polymer shows peaks consistent to the addition product from the model compound of the expected product, indicating successful addition of polyoctene-Zn to the aldehyde. These peaks are absent in the polymer from the comparative run.

Figure 19:
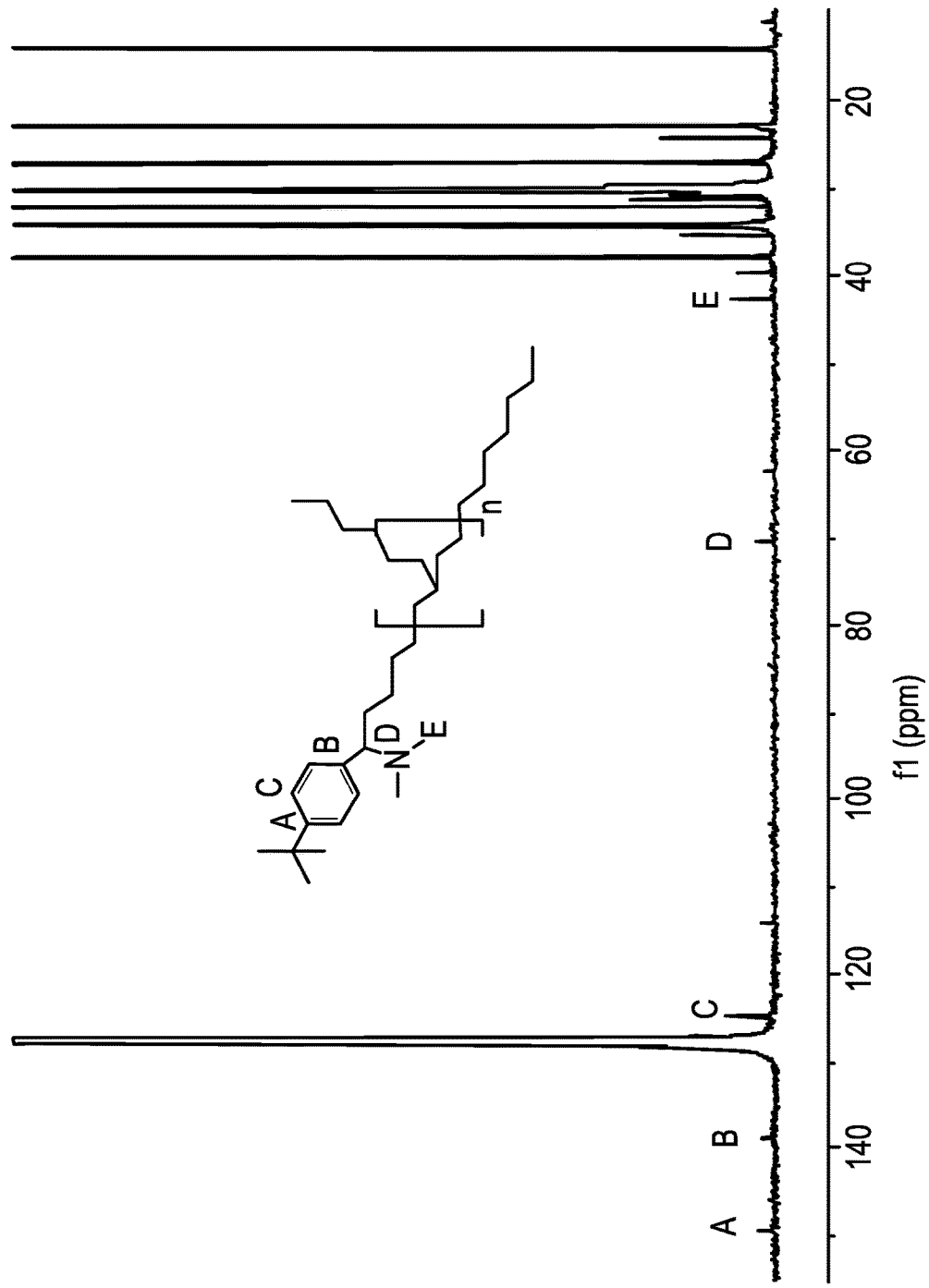
FIG. 19 provides the $^{13}C$ NMR spectrum of functionalized ethylene-octene copolymer in benzene at 60° C.

As a further, non-limiting example, the present inventors attempted to functionalize ethylene-octene copolymer made in a batch reactor. A one gallon (3.79 L) stirred autoclave reactor was charged with ca 1.3 kg of Isopar™ E mixed alkanes solvent. The reactor was heated to 120° C. and charged with 250 grams of 1-octene and ca. 150 grams of ethylene to maintain the total pressure at ca. 430 psig. Diethyl-zinc (1.92 mmol) was added as a chain shuttling agent. The catalyst mixture was prepared in a drybox under an inert atmosphere by mixing the catalyst and co-catalyst at a molar ratio of (E)-((2,6-diisopropylphenyl)(2-methyl-3-(octylimino)butan-2-yl)amino)trimethyl hafnium catalyst: bis(hydrogenated tallow alkyl)methylammonium tetrakis (pentafluorophenyl)borate:MMAO=1:1.2:10, with additional solvent to give a total volume of about 17 mL. The activated catalyst mixture was quickly injected into the reactor. After 10 minutes, 10 ml of a $(NMe_2)_2TiCl_2$ solution in toluene (0.193 M, 1.93 mmol) was injected followed by 5 ml of tBu-benzaldehyde solution in toluene (0.77 M, 3.85 mmol). The reaction was continued for 20 minutes, then the solution was transferred into a nitrogen-purged resin kettle. After the solvent was evaporated, the polymer was re-dissolved in toluene and precipitated in large amount of methanol. The final polymer was collected and thoroughly dried in a vacuum oven. The $^{13}C$ NMR analysis of the polymer is shown in FIG. 19, suggesting the presence of a terminal amine functional group.

Accordingly, in certain embodiments, the present disclosure relates to a simple, one pot reaction for synthesizing functional polymers through addition of polymeryl-zinc to aldehydes in the presence of a Lewis acid with the formula $(R_2N)_nMX_{4-n}$ that is adaptable to existing solution processes. In other words, the simple, one-pot process of the present disclosure demonstrates the transfer of polymeryl groups to the aldehyde without the undesired reductive elimination reaction, is facile at high temperatures, can be completed in a reasonably short amount of time, and exhibits the reaction of both polymeryl R' groups of $ZnR'_2$. Additionally, as discussed above in connection with the functionalization of alkyl-zinc, the simple, one-pot reaction of the present disclosure is not limited to the functionalization of polymeryl-zinc by addition of amino groups from a Lewis acid with the formula $(R_2N)_nMX_{4-n}$. For example, other functional groups may be added to the polymer chain via inclusion of the functional groups on the aldehyde. Accordingly, the simple, one-pot reaction of the present disclosure can be utilized to add various functional groups to polymer chains. Exemplary functional groups include amine (primary, secondary, tertiary, quat. salt), vinyl, allyloxy, and styrryl groups.

Functionalization of polymeryl-zinc by employing polymeryl-zinc and aldehydes in the presence of a Lewis acid with the formula $(R_2N)_nMX_{4-n}$ is not limited to the functionalization of polyoctene homopolymers and ethylene-octene co-polymers described above. In further embodiments, the simple, one-pot process of the present disclosure may be utilized to functionalize any polymeryl-zinc composition formed by any polymerization of suitable addition polymerizable monomers via any polymerization method known to a person of ordinary skill in the art. In further embodiments, the present disclosure provides for a facile, one-pot reaction for preparing any functional polymer or polyolefin that a person of ordinary skill in the art would reasonable expect to form through the chemistry of the facile, one-pot reaction. Non-limiting examples of functional polymers or polyolefins that may be prepared by the simple, one-pot reaction of the present disclosure provides include functional polymers or polyolefins containing functional groups, polymers or polyolefins containing terminal functional groups on one end or both ends, telechelic polymers containing terminal functional groups on both ends possessing the same functionality, olefin/non-olefin diblock copolymers containing functional groups, and hard-soft-hard triblock copolymers containing functional groups.

Further, non-limiting examples of functional polymers or polyolefins prepared by the simple, one-pot reaction of the present disclosure are provided in FIG. 20. In each of reactions (1)-(4) of FIG. 20, the polymeryl-zinc composition may be prepared by a polymerization process, the polymerization process comprising: contacting at least one addition polymerizable monomer with a catalyst composition under polymerization conditions, the catalyst composition comprising the contact product of at least one catalyst precursor, at least one co-catalyst, and at least one chain shuttling agent. FIG. 20, reaction (1), demonstrates the formation of polymers or polyolefins with various terminal functional groups ("FG") via functionalization of polymeryl-zinc. FIG. 20, reaction (2), demonstrates the formation of telechelic polymers via functionalization of polymeryl-zinc compositions, wherein the chain shuttling agent in the polymerization process may be a multi- or dual-headed chain shuttling agent. In this regard, the multi- or dual-headed chain shuttling agent may be prepared by any known or novel methods for forming such a chain shuttling agent. Accordingly, in further embodiments, the simple, one-pot process of the present disclosure may be combined with a process for preparing a multi- or dual-headed chain shuttling agent. FIG. 20, reaction (3), demonstrates the formation of functionalized polymers or polyolefins. FIG. 20, reaction (4), demonstrates the formation of functionalized multi-block copolymers containing "hard and soft" blocks.

What is claimed is:

1. A process for producing a functional polymer comprising:
    reacting an aldehyde with a zinc composition in the presence of a Lewis acid having the formula $(R_2N)_n MX_{4-n}$, wherein
    the zinc composition has the formula $ZnR'_2$ or $R^1Zn[R'Zn—]_yR^1$, and wherein:
    n is an integer from 1 to 3;
    X is Cl, Br, or I;
    R is a $C_{1-10}$ hydrocarbon;
    M is a Group 4 metal;
    R' in each occurrence is a polymer composition;
    $R^1$ in each occurrence is independently selected from a polymer composition, alkyl, hydrogen, halide, amide, hydrocarbyl, hydrocarbylamide, dihydrocarbylamide, hydrocarbyloxide, hydrocarbylsulfide, dihydrocarbylphosphido, tri(hydrocarbyl)silyl; any hydrocarbyl group being optionally substituted with at least one halide, amide, hydrocarbylamide, dihydrocarbylamide, or hydrocarbyloxide; and each carbon-containing $R^1$ having from 1 to 50 carbon atoms, inclusive; and
    Y, on average, in each occurrence is a number from 1-150, inclusive.

2. The process of claim 1, wherein the Lewis acid is bis(dimethylamido)dichlorotitanium.

3. The process of claim 1, wherein the polymer composition is formed by a polymerization process, the polymerization process comprising: contacting at least one addition polymerizable monomer with a catalyst composition under polymerization conditions, the catalyst composition comprising the contact product of at least one catalyst precursor, at least one co-catalyst, and at least one chain shuttling agent.

4. The process of claim 3, wherein the zinc composition has the formula $R^1Zn[R'Zn-]_rR^1$ and the at least one chain shuttling agent is a multi- or dual-headed chain shuttling agent.

5. The process of claim 1, wherein the reacting step is conducted at a temperature greater than 70° C.

6. The process of claim 1, wherein the reacting step is completed in less than 40 minutes.

7. The process of claim 1, wherein the functional polymer includes at least one amino group.

8. The process of claim 1, wherein the aldehyde includes at least one functional group.

9. The process of claim 8, wherein the at least one functional group is a vinyl, allyloxy, or styryl group.

10. The process of claim 9, wherein the functional polymer includes at least one amino group and a further functional group, wherein the further functional group is a vinyl, allyloxy, or styryl group.

11. The process of claim 1, wherein the zinc composition has the formula $ZnR'_2$, and wherein both R' groups of $ZnR'_2$ are reacted in the reacting step.

12. The process of claim 4, wherein the functional polymer is a telechelic polymer.

\* \* \* \* \*